US006413547B1

(12) United States Patent
Bennett et al.

(10) Patent No.: US 6,413,547 B1
(45) Date of Patent: Jul. 2, 2002

(54) LIQUID CRYSTAL FORMS OF CYCLOSPORIN

(75) Inventors: David B. Bennett, San Jose; Kirsten M. Cabot, San Francisco; Linda C. Foster, Mountain View; David Lechuga-Ballesteros, Santa Clara; John S. Patton, Portola Valley; Trixie K. Tan, Daly City, all of CA (US)

(73) Assignee: Inhale Therapeutic Systems, Inc., San Carlos, CA (US)

( * ) Notice: Subject to any disclaimer, the term of this patent is extended or adjusted under 35 U.S.C. 154(b) by 0 days.

(21) Appl. No.: 09/248,416

(22) Filed: Feb. 11, 1999

Related U.S. Application Data

(60) Provisional application No. 60/075,422, filed on Feb. 20, 1998.

(51) Int. Cl.[7] .............................. A61K 9/14; A61L 9/04
(52) U.S. Cl. ........................ 424/489; 424/45; 424/46; 514/886; 514/951
(58) Field of Search ............................... 424/489, 455, 424/46, 456, 457, 45; 514/886, 951

(56) References Cited

U.S. PATENT DOCUMENTS

| | | | | |
|---|---|---|---|---|
| 5,051,402 A | * | 9/1991 | Kurihara et al. | 514/11 |
| 5,342,625 A | * | 8/1994 | Hauer et al. | 424/455 |
| 5,458,135 A | | 10/1995 | Patton et al. | |

FOREIGN PATENT DOCUMENTS

| | | | |
|---|---|---|---|
| EP | 504760 | * | 3/1992 |
| EP | 92014426.9 | | 5/1992 |
| EP | 0 504 760 | | 9/1992 |
| GB | 8829556.3 | | 5/1988 |
| WO | WO95 32726 | | 12/1995 |
| WO | WO96 06598 | | 3/1996 |
| WO | WO96/09085 | | 3/1996 |
| WO | WO97/41833 | | 11/1997 |
| WO | WO98 10747 | | 3/1998 |

OTHER PUBLICATIONS

Aramaki et al. "Effect of Temperature on the Phase Behavior of Ionic–Nonionic Microemusions," J. Colloid Interface Sci. Dec. 1, 1997, 196(1), pp. 74–78, abstract.*

Trotta et al. "Pseudo–ternary phase diagrams of lecithin–based microemulsions:influence of monoalkylphosphates," J. Pharm. Pharmacol. Jun. 1995, 47(6), pp 451–454, abstract.*

Brown et al. "Liquid Crystals," Chemical and Engineering News, Jan. 31, 1983, pp 24–38.*

O'Riordan et al., "Production of an Aeorosl of Cyclosporin as a Prelude to Clinical Studies," J. Aeorosl Med., vol. 5 (No. 3), p. 171–177, (1992).

O'Riordan et al., "Delivery and Distribution of Aerosolized Cyclosporine in Lung Allograft Recipients," Am. J. Respir. Crit. Care Med., p. 516–521, (1995).

Iacono et al., "Aerosolized Cyclosporine in Lung Recipients with Refractory Chronic Rejection," Am. J. Respir. Crit. Care Med., p. 1451–1455, (1996).

Lock et al., "Double–Blind Placebo Controlled Study of Cyclosporin A as a Corticosteroid–Sparing Agent in Corticosteroid–Dependent Asthma," Am. J. Respir. Crit. Care Med., p. 509–514, (1996).

(List continued on next page.)

Primary Examiner—James M. Spear
Assistant Examiner—Blessing Fubara
(74) Attorney, Agent, or Firm—Susan T. Evans; Felissa H. Cagan

(57) ABSTRACT

This invention relates to novel, liquid crystal forms of the cyclic peptide cyclosporin and to novel powder formulations of cyclosporin prepared using this novel liquid crystal form of the drug. Methods for preparing and using these formulations are also provided. In particular, the present invention relates to dispersible spray dried particles of cyclosporin suitable for pulmonary delivery.

24 Claims, 12 Drawing Sheets

CALCULATED X-RAY POWDER DIFFRACTION FOR CsA III (ORTHORHOMBIC)

OTHER PUBLICATIONS

Alexander et al., "Clinical Response to Cyclosporin in Chronic Severe Asthma is Associated with Reduction in Serum Soluble Interleukin–2 Receptor Concentrations," Eur. Respir. J., p. 574–578, (1995).

Alexander et al., "Trial of Cyclosporin in Corticosteroid–Dependent Chronic Severe Asthma, " Lancet, p. 324–328, (1992).

Petcher et al., "Crystal and Molecular Structure of an Iodo–Derivative of the Cyclic Undercapaptide Cyclosporin A," Helvitica Chimica Acta, vol. 59 (No. 5), p. 1480–1488.

Strong et al., "Effects of Low and High Density Lipoproteins on Renal Cyclosporine G Disposition in the Isolated Perfused Rat Kidney," Pharm Res, vol. 14 (No. 10), p. 1466–1471, (1976).

Burckart et al., "Inhalation Delivery of Therapeutic Peptides and Proteins," Marcel Dekker, NY, p. 281–299, (1997).

Vadiei et al., "Pharmacokinetic and Pharmacodynamic Evaluation of Liposomal Cyclosporine," Intl. J. Pharm, 57: p. 125–131, (1989).

Vadiei et al., "In Vitro Evaluation of Liposomal Cyclosporine," Intl. J. Pharm, p. 133–138, (1989).

Waldrep et al., "Cyclosporin A Liposome Aerosol: Particle Size and Calculated Respiratory Deposition," Intl. J. Pharm, p. 205–212, (1993).

Al–Angary et al., "Characterization, Stability and in Vivo Targeting of Liposomal Formulations Containing Cyclosporin," Intl. J. of Pharm, p. 221–225, (1995).

Loosli et al., "The Conformation of Cyclosporin A in the Crystal and in Solution," Helvetica Chemica Acta, p. 682–704, (1985).

Matha et al., "The Story of the Czech Cyclosporin A," p. 28.

Knott et al., "Neutron Structure of the Immunosuppressant Cyclosporin–A," Acta Cryst, p. 1528–1533, (1990).

The Merck Index, Twelth Edition, p. 464–465 (1990).

Guzman et al., "Formation Characterization of Cyclosporine—Loaded nanoparticles" J. of Pharm Sci, 82:5.

Med. Ad. News, Feb. 1996, p. 7–10.

Physician's Desk Reference, 52nd Ed. 1898–1901 (1998).

Oliyai et al., "Kinetics of Acid–Catalyzed Degradation of Cyclosporin A and its Analogs in Aqueous Solutions" Peptide and Protein Res. 43:239–247 (1994).

Oliyai et al., Kinetics and Mechanism of Isomerization of Cyclosporin A, Pharm. Res. 9(5): 617–622 (1992).

* cited by examiner

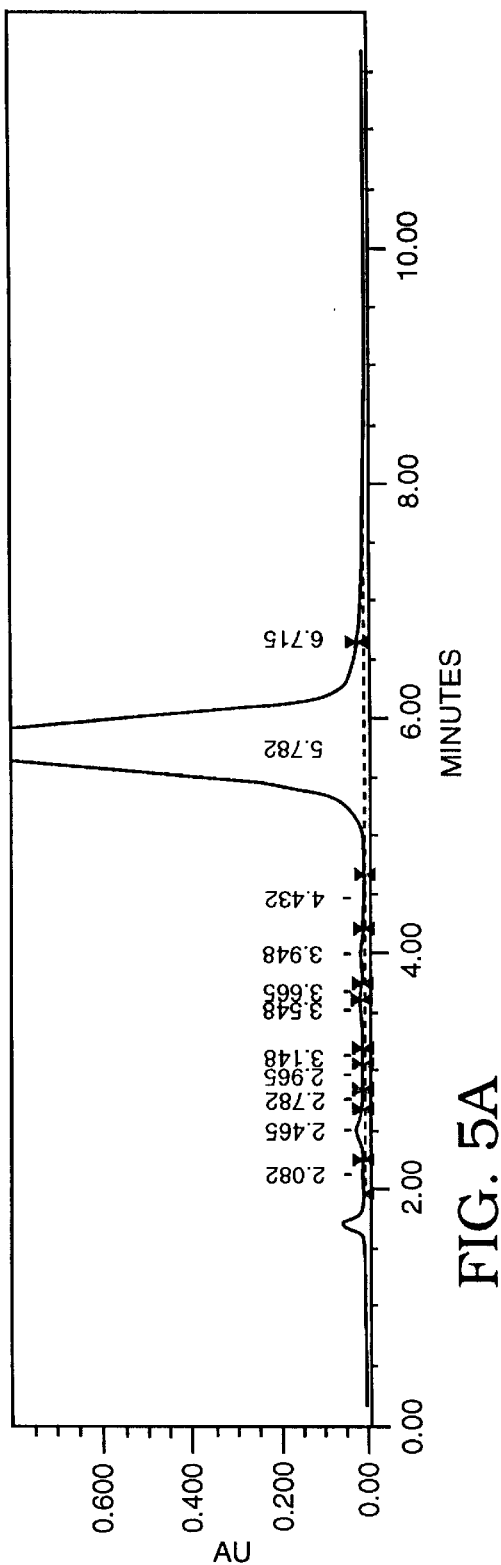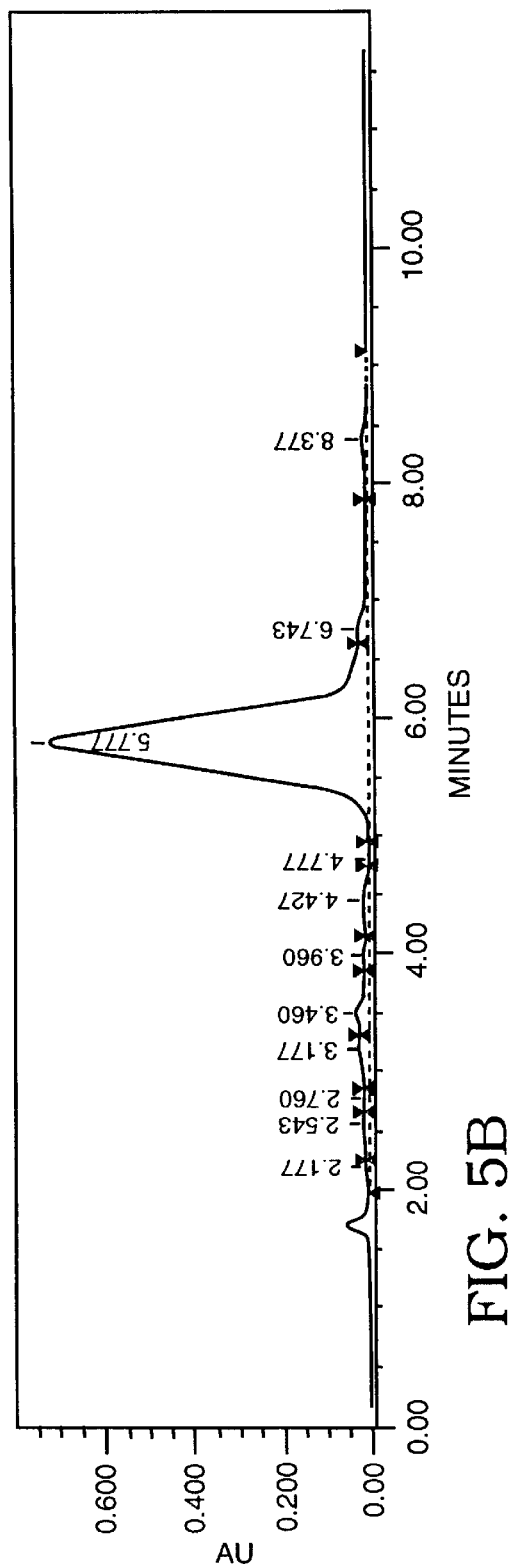
FIG. 5A
FIG. 5B

LIQUID CRYSTAL FORMS OF CYCLOSPORIN

This Application claims benefit of provisional Application No. 60/075,422 filed Feb. 20, 1998.

FIELD OF THE INVENTION

This invention relates to a liquid crystal form of the cyclic peptide cyclosporin and to powder formulations of cyclosporin prepared using this novel liquid crystal form of the drug. Methods for preparing and using these formulations are also provided. In particular, the present invention relates to dispersible spray dried particles of cyclosporin suitable for pulmonary delivery.

BACKGROUND OF THE INVENTION

The cyclosporins are a group of non-polar oligopeptides with immunosuppressant activity. Cyclosporin A, also known as cyclosporine, is the major known cyclosporin, with the structure of cyclosporins B through I also being known (The Merck Index, Twelfth Edition, 464–465 (1996)). A number of synthetic cyclosporin analogs have been prepared. (Id.)

Cyclosporin A is an orally active immunosuppressive drug that has been used for immune suppression since the mid-1980's (Guzman et al., J. of Pharm Sci, 82:5) 496–506 (1993)). It has become the mainstay of organ transplant therapy as prophylaxis against organ rejection. The original cyclosporine product for this use, Sandimmune by Sandoz, is formulated in corn oil and designed for oral delivery, however, bioavailability from the gastrointestinal tract tends to be low and somewhat erratic. (Id.) Recently, Sandoz has begun marketing an improved proprietary oral formulation (Neoral) that is claimed to be more reliable than the original (Med. Ad. News, Feb 1996, 7–10). Cyclosporin A causes kidney and liver toxicity at high doses when delivered orally and tolerability must always be monitored along with clinical assessments of rejection (Physician's Desk Reference, $52^{nd}$ Ed, 1891–1901 (1998)).

In order to avoid the complications associated with oral delivery, and, in particular, to prevent lung transplant rejection, it may be desirable to deliver cyclosporin directly to the lungs. In fact, nebulized cyclosporin A appears to be efficacious in preventing lung transplant rejection using aerosolized liquid ethanol and polyethylene glycol cyclosporine formulations (Burckart, et al., *Inhalation Delivery of Therapeutic Peptides and Proteins*, Marcel Dekker, N.Y., pp 281–299 (1997)). Nebulized cycisporin A also appears to lower oral cortico-steroid dependency in asthma (Morley, et al., *Cyclosporin Form for Pulmonary Administration*, European Patent Application No. 92104426.9 (1992)). Liposomal cyclosporine has also been administered as an aerosol using a nebulizer (Waldrep, et al., *Cyclosporin A Liposome Aerosol: Particle Size and Calculated Respiratory Deposition*, Intl. J. Pharm. 97:205–212 (1993)). The aim of such formulations has been to decrease toxicity compared to conventional oral formulations and to provide an alternative to nebulized solutions containing cosolvents.

Nebulized solution delivery of cyclosporin suffers from limited drug solubility in aqueous based vehicles. Further, there are safety concerns surrounding nebulization of organic vehicles. Delivery of nebulized solutions and suspensions both suffer from low drug delivery efficiency from commercial nebulizers. Aerosolization of cyclosporin A (CsA) with MDI's would involve a solution of CsA in propellant(s) (chlorofluorocarbon or non-chlorofluorocarbon propellants) or the use of finely divided CsA suspended in propellant(s). Poor drug delivery efficiency and low drug-carrying payload capacity make MDI's an inconvenient means of aerosol delivery for human dosing regimens that may require 1 mg to 20 mg of CsA delivered per day to the lung.

In view of the difficulty of delivering a solution of cyclosporin by inhalation, it may be desirable to deliver cyclosporin as a dry powder. The ability to deliver pharmaceutical compositions as dry powders, however, is problematic in certain respects. The dosage of many pharmaceutical compositions is often critical, so it is desirable that dry powder delivery systems be able to accurately, precisely and reliably deliver the intended amount of drug. It is also essential that dry powders for pulmonary delivery be readily dispersible in order to assure adequate distribution and systemic absorption. Because CsA can cause gingivitis, it is important that oropharyngeal deposition be minimized.

SUMMARY OF THE INVENTION

The present invention provides a novel liquid crystal form of cyclosporin not previously known. This novel form is thermotropic liquid crystal cyclosporin. It has unexpectedly been found that spray drying organic solutions containing cyclosporin, in particular cyclosporin A (CsA), under specific conditions, results in this novel form of cyclosporin. Spray drying of organic solutions containing cyclosporin produces powders where the particulate cyclosporin exhibits a lack of 3-dimensional (3-d) order as determined by powder X-ray diffraction (PXRD) and also exhibits 2-d order when analyzed by small angle X-ray scattering (SAXS). Further, it exhibits a phase change from solid to liquid over a narrow temperature range with a step-wise change in heat capacity, i.e., a glass transition-like melt. This form of cyclosporin is liquid crystal cyclosporin. The process conditions for spray drying may be varied within certain limits to achieve very narrow particle size distributions that make the powders especially suitable for efficient delivery by oral inhalation. These powders have high delivery efficiency when aerosolized with a dry powder inhaler and have demonstrated physical, chemical, and aerosol stability over prolonged periods of high temperature and high humidity.

In one aspect the invention provides liquid crystal cyclosporin. In particular, the liquid crystal form of cyclosporin A is provided.

In another aspect the invention provides dispersible powder formulations of liquid crystal cyclosporin for pulmonary delivery. In particular, cyclosporin-based dispersible powder formulations which are spray dried from cyclosporin and, optionally, excipient, in a solvent are provided, as are methods for making these formulations. Spray dried cyclosporin A powders are specifically provided.

In a further aspect the invention provides methods for treating a subject suffering from or subject to a condition which may be alleviated or prevented by the administration of cyclosporin comprising administering the dispersible powder cyclosporin formulations described above. In particular, methods to alleviate or prevent lung diseases or conditions which affect the lung are provided. Cyclosporin may be used as an anti-inflammatory, immunosuppressive or anti-asthmatic agent.

BRIEF DESCRIPTION OF THE DRAWINGS

FIGS. 5A, 5B and 5C illustrate BPLC analysis of spray dried cyclosporin A at accelerated storage conditions of 110° C. for 196 hours, 140° C. for 50 hours and 210° C. for 10 minutes, respectively.

DETAILED DESCRIPTION OF THE INVENTION

Figure 1A:
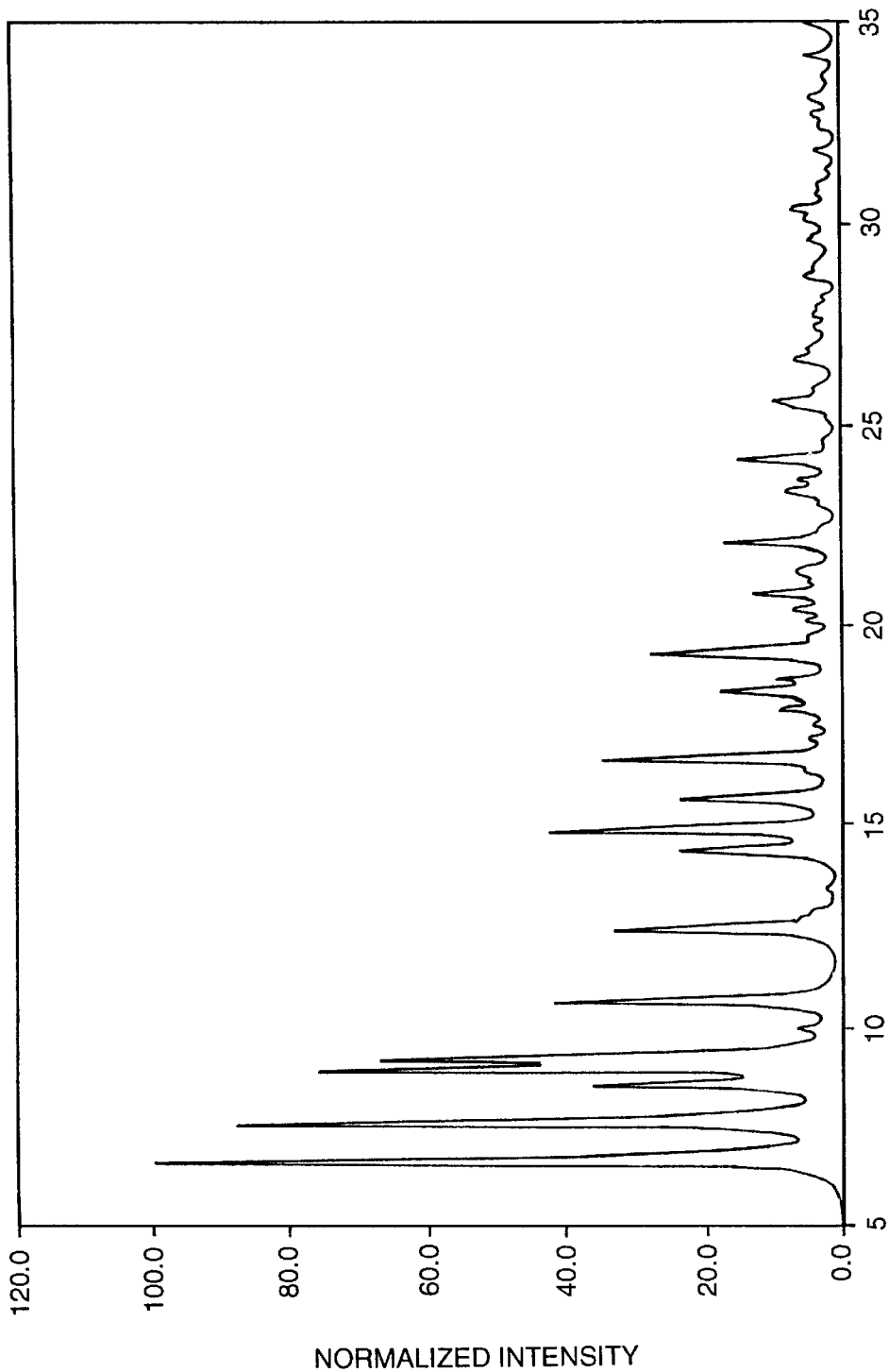
FIGS. 1A through 1C illustrate the difference in X-ray powder diffraction patterns between two of the known crystalline forms of cyclosporine (non-solvated orthorhombic (FIG. 1A) and dihydrate tetragonal (FIG. 1B)) and the novel thermotropic liquid crystal form of cyclosporine provided by the present invention (FIG. 1C).

The present invention is based at least in part on the discovery of a novel, thermotropic liquid crystal form of cyclosporin, particularly cyclosporin A. This liquid crystal form of cyclosporin may be formulated as a dispersible powder by spray drying from organic solvents. The cyclosporin-based compositions are suitable for pulmonary delivery due to their dispersibility characteristics. The compositions of the invention are readily aerosolized and presented to the deep lung of a host when delivered by a dry powder inhaler. The powder formulations of the present invention retain stability, are readily dispersible for pulmonary delivery and allow for unit dose packaging.

The invention consists, in part, of compositions comprising cyclosporin in dispersible powder formulations. The use of particles of a certain size range allows for delivery of cyclosporin to the alveolar area of the lungs (i.e., to the deep lung). Optionally, the powder formulations of the present invention may contain stabilizers and excipients such as buffer salts, sugars, tonicifiers, preservatives and antioxidants. The compositions of the present invention are useful in pulmonary dry powder drug delivery systems, including but not limited to those disclosed in U.S. Pat. No. 5,458,135 and International Patent Publication WO96/09085.

The solid state forms of CsA that have previously been reported are described in Table 1.

TABLE 1

Solid State Forms of Cyclosporin A

| Crystal System | Solvation | Melting Range (° C.) | Space Group | Unit Cell Dimensions (Å) | | | Reference |
| --- | --- | --- | --- | --- | --- | --- | --- |
| | | | | a | b | c | |
| tetragonal | dihydrate | 140–150 | P4$_1$ | 13.837 | 13.387 | 41.242 | 1, 2 |
| tetragonal | non-solvated | nr | P4$_1$ | nr | nr | nr | 3 |
| orthorhombic | di-(di-isopropyl ether) | ~150 | P2$_1$2$_1$2$_1$ | 12.5 | 22.9 | 23.4 | 1 |
| orthorhombic | non-solvated | 180–195 | P2$_1$2$_1$2$_1$ | 12.7 | 15.7 | 36.3 | 1, 3 |
| orthorhombic | monohydrate | nr | P2$_1$2$_1$2$_1$ | 12.5 | 22.9 | 28.4 | 4 |
| amorphous | n/a | n/a | n/a | n/a | n/a | n/a | 3 | nr = not reported
n/a = not applicable

REFERENCES

1. Giron, et al., *Orthorhombic Cyclosporin Crystals*, UK Patent Application No. 8829556.3 (1988).
2. Loosli, et al., *The Conformation of Cyclosporin A in the Crystal and in Solution*, Helvetica Chemica Acta, 68:682–704 (1985).
3. Matha, et al., *The Story of the Czech Cyclosporin A*, 28 pp.
4. Knott, et al., *Neutron Structure of the Immunosuppressant Cyclosporin-A*, Acta Cryst., C46:1528–1533 (1990).

Tetragonal and orthorhombic crystal forms of CsA exhibit high melting points and have characteristic sharp diffraction peaks when analyzed by PXRD and are birefringent to polarized light. Amorphous materials, unlike liquid crystals, have no peaks by SAXS and are not birefringent to polarized light. Liquid crystals show a distinct melt over a narrow temperature range unlike amorphous glasses which show no such melt. An amorphous form of CsA has been mentioned without report of its physicochemical properties (Morley, et al., European Patent Application No. 92104426.9 (1992)).

Figure 1B:
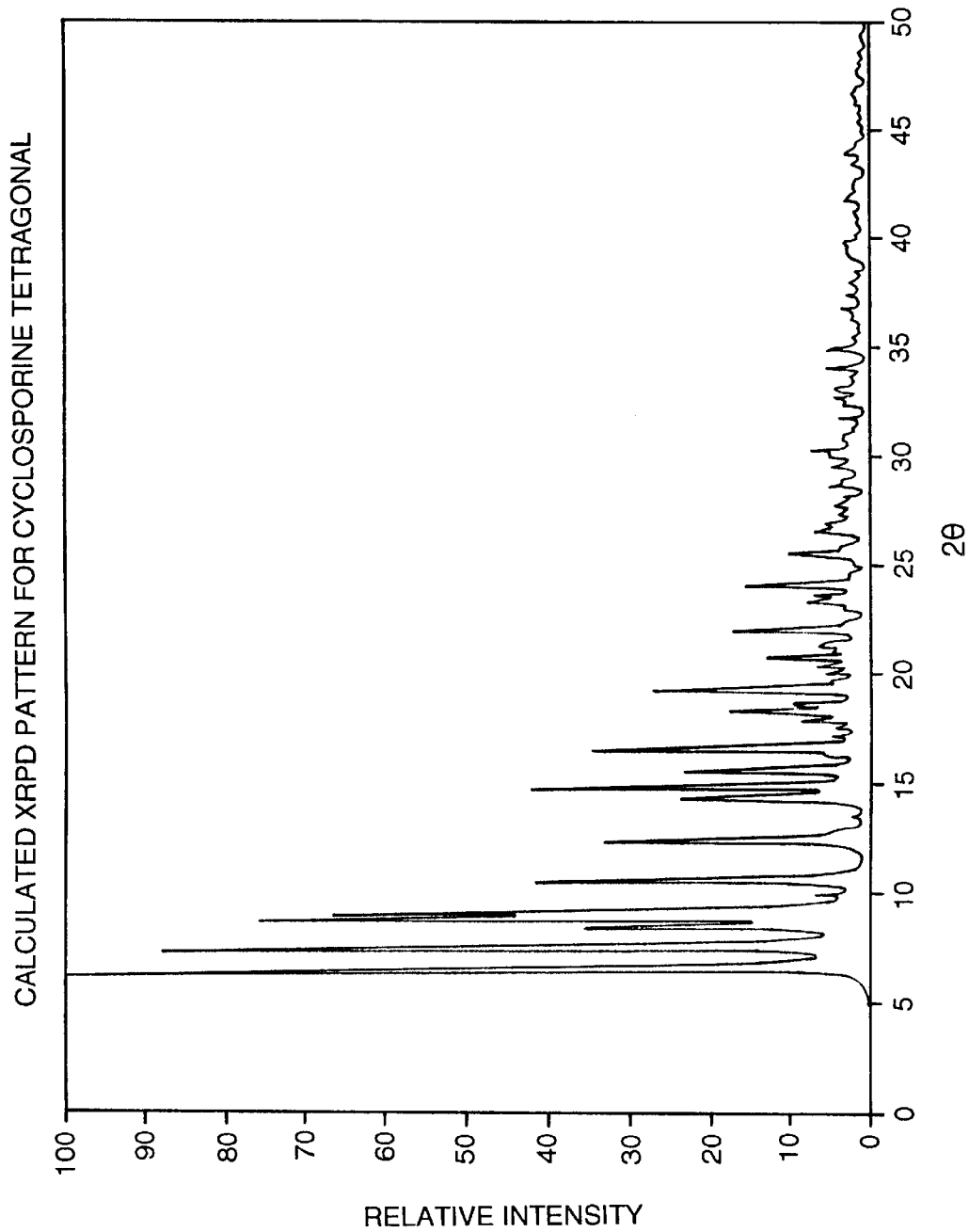
Figure 1C:
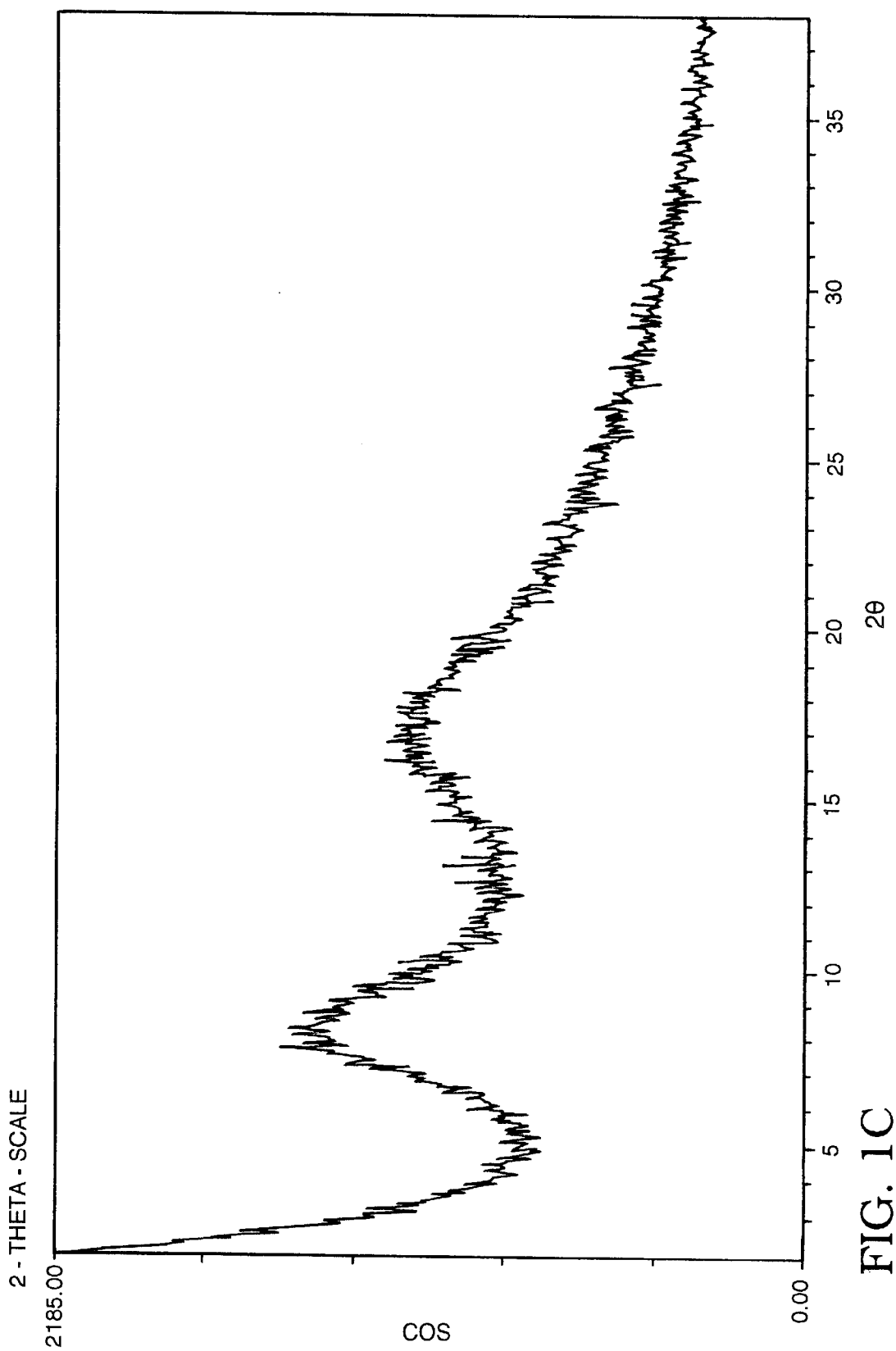
Figure 3:
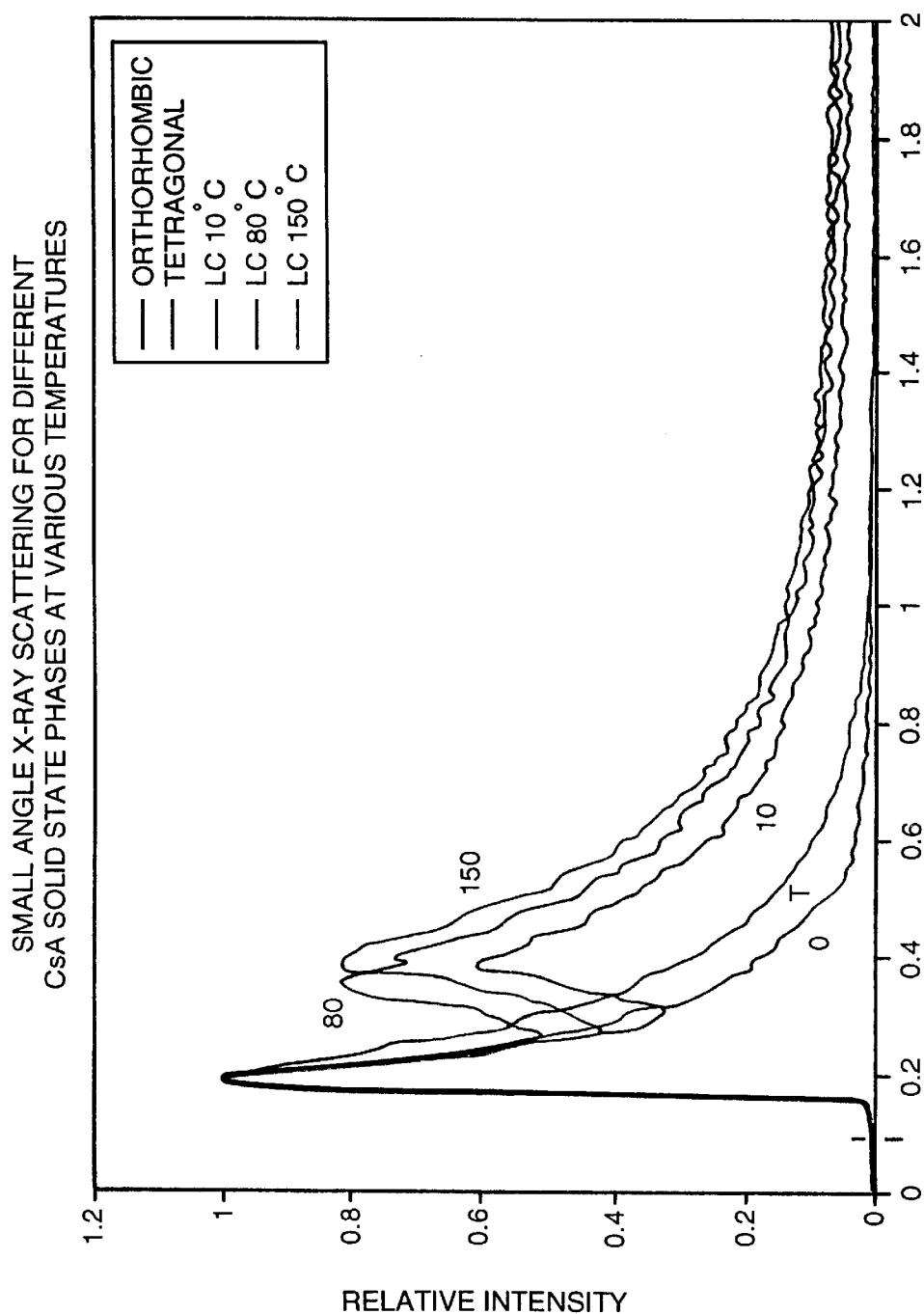
FIG. 3 presents the small angle X-ray scattering data for orthorhombic and tetragonal crystalline cyclosporine and for spray dried liquid crystal cyclosporine at 10, 80 and 150° C.

We have discovered that CsA powders prepared by organic solvent spray drying can be designed such that they are not of the orthorhombic or tetragonal crystal forms. Indeed, no sharp diffraction peaks indicative of 3-dimensional order are observed by PXRD of the spray dried powders (FIG. 1C). However, the spray dried powders do exhibit 2-dimensional order when analyzed by SAXS, indicative of a liquid crystal form (FIG. 3).

Figure 2A:
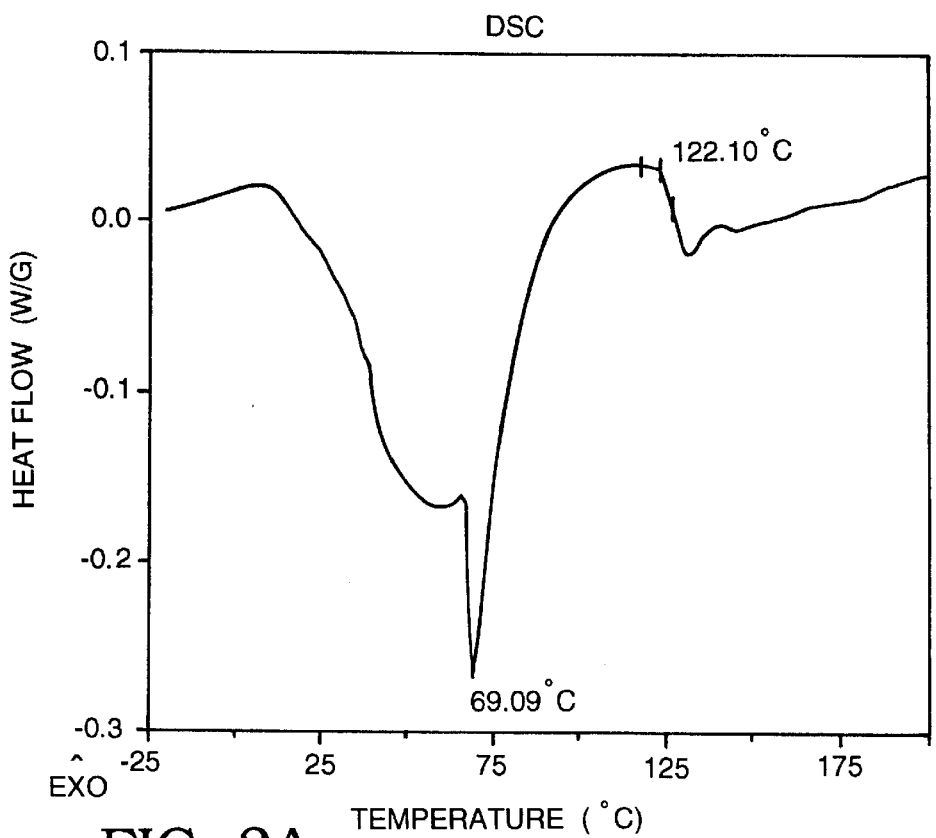
FIG. 2A illustrates a representative open pan differential scanning calorimetry (DSC) tracing and FIG. 2B illustrates a representative closed pan DSC tracing for the thermotropic liquid crystal form of cyclosporine of the present invention.

Furthermore, the CsA powders prepared by organic solvent spray drying also demonstrated a distinct endotherm between 0–75° C. when analyzed by differential scanning calorimetry (DSC) at 10°/min in an open pan (FIG. 2A). Since the physical nature of the powders does not change (not a melt) through that temperature range and because the endotherm is absent in the closed pan DSC trace (FIG. 2B), the transition is believed to be due to solvent evaporation. A melt occurs beginning at about 120° C. when analyzed by hotstage microscopy at 2°/minute. The DSC thermogram at the same heating rate shows a step-wise change in heat capacity (Cp) (a Tg-like transition) at that temperature. Typically, 3-d ordered crystals do not exhibit a step-wise Cp change going from solid to liquid. Furthermore, dielectric analysis is consistent with DSC results and confirms that the transition observed at ~120° C. is a second order transition, as it is demonstrated by the observed frequency dependency.

A. Definitions

As used herein the following terms have the following meanings:

The terms "dispersibility" or "dispersible" mean a dry powder having a moisture and/or residual solvent content of less than about 10% by weight (% w), usually below about 5% w and preferably less than about 3% w and often less than about 1% w; a particle size of between 0.1 and 15 $\mu$m, often between 0.2 $\mu$m and 10 $\mu$m, usually about 0.4 to 5 $\mu$m mass median diameter (MMD), preferably about 1 to 4 $\mu$m MMD and most preferably 1 to 2 $\mu$m MMD; a delivered dose of greater than about 30%, usually greater than about 40%, preferably greater than about 50% and most preferably greater than about 60%; and an aerosol particle size distribution of about 1–5 $\mu$m mass median aerodynamic diameter (MMAD), usually about 1.5–4.5 $\mu$m MMAD and preferably about 1.5–4.0 $\mu$m MMAD, or with at least about 40% (preferably at least about 50%) of the particles less than about 3.3 $\mu$m in diameter.

The term "cyclosporin" means any of the group of non-polar cyclic oligopeptides with immunosuppressant activity and includes known cyclosporins A through I. In particular, this term includes cyclosporin A, also known as cyclosporine. Synthetically produced, naturally-derived or purified and recombinantly produced moieties are included, as are analogs, derivatives, agonists, antagonists and pharmaceutically acceptable salts of any of these. The term also includes cyclosporins which have D-amino acids, modified, derivatized or non-naturally occurring amino acids in the D- or L-configuration and/or peptomimetic or prodrug units as part of their structure.

A thermotropic liquid crystal is a state of matter distinct from the amorphous and 3-dimensional crystalline states and characterized by the existence of long range order in one (nematic) or two (smectic) dimensions in the absence of solvent. An amorphous phase lacks long-range order and a 3-dimensional crystalline phase contains 3-dimensional long-range order.

The term "powder" means a composition that consists of finely dispersed solid particles that are free flowing and capable of being readily dispersed in an inhalation device and subsequently inhaled by a subject so that the particles reach the spaces of the deep lung to permit deposition in the alveoli. Thus, the powder is said to be "respirable." The terms "pharmaceutical excipient" or "additive" mean compounds which stabilize cyclosporin and/or improve powder aerosol performance and stability. The types of excipients useful in the present invention include buffer salts, sugars, tonicifiers, preservatives and anti-oxidants, and the like.

The term "physically stable" or physical stability" intends a composition that does not show a change in phase over time. The term "chemically stable" or "chemical stability" means that the composition shows less than 10% and, preferably, less than 5% total degradation in 2 years at room temperature at the storage conditions specified. "Aerosol stability" means that the aerosol composition shows no statistical change in delivered dose efficiency with time.

The term "subject" includes any human or animal species in need of cyclosporin for treatment or prophylaxis of conditions for which pulmonary delivery of cyclosporin would be efficacious.

B. Compositions

The present invention is drawn to liquid crystal forms of cyclosporin and to dispersible cyclosporin-containing powder compositions suitable for pulmonary delivery formed by spray drying from organic solvents. The dispersible powder compositions comprise a therapeutically effective amount of cyclosporin, optionally in combination with a pharmaceutically acceptable carrier or excipient.

Spray drying is a process that utilizes high temperatures and high-carrier gas flow rates to rapidly evaporate solvents from an atomized solution that contains dissolved solutes. The solvent evaporates to leave a solid particle. The size of the particle is dependent upon the conditions of the spray drying process (e.g., solids content of solution, pressure of atomization gas, design of atomizer nozzle and design of cyclone collector). Control of particle size and particle size distribution is important for efficient inhalation delivery to the airways and the deep lung. The mass median diameter (MMD) of the particles should preferably be between 1 and 2 $\mu$m, with 100% of the particles less than 15 $\mu$m.

It can also be difficult to control particle size and particle size distribution in compositions produced by spray drying. For pulmonary delivery it is critical that the average particle size be maintained in a respirable range and that the amount of the composition comprising particles outside the target size range be minimized. Moreover, it can sometimes be difficult to achieve a desired low residual solvent and/or moisture content required for physical and chemical stability in the final particulate product, particularly in an economic manner. Useful methods are disclosed, for example, in International Patent Application No. PCT/US97/07779, the disclosure of which is incorporated herein by reference in its entirety.

Cyclosporin, including cyclosporin A (CsA) is very hydrophobic and is practically insoluble (<6 $\mu$g/mL) in aqueous vehicles. Organic solvents with boiling points less than 200° C., preferably less than 150° C., and most preferably less than 100° C. should be used to obtain powders with low residual solvent. The preferred solvents for making spray dried cyclosporin (including CsA) powders include, but are not limited to, ethanol, acetone, acetonitrile, methanol, isopropanol, and methylene chloride, either alone or in combination or in cosolvent systems. Pharmaceutically acceptable protic solvents with low dielectric constants are more preferred (e.g., ethanol is preferred over methanol).

Solvent mixtures with less than 50%, preferably less than 25%, and most preferably with 10% or less water by volume may also be employed for spray drying cyclosporin. Use of water in the solvent mixture allows the incorporation of water-soluble excipients into the CsA particles, however non-aqueous systems are preferred. Water-soluble excipients useful in the present invention include, but are not limited to, buffer salts (e.g., citric acid/sodium citrate), natural and synthetic sugars as bulking agents (e.g., lactose, mannitol), tonicifiers (e.g., sodium chloride), and preservatives and anti-oxidants (e.g., ascorbic acid/sodium ascorbate).

Pharmaceutical excipients and/or additives generally useful in the present invention include suitable pH adjusters or buffers such as organic salts prepared from organic acids and bases, such as sodium citrate, glycine, sodium tartrate, sodium lactate, tromethamine and the like. Proteins (e.g., HSA, recombinant human albumin (rHA), gelatin and casein), peptides (e.g., aspartame) and amino acids (e.g., alanine, glycine, arginine, glutamic acid and aspartic acid) which improve dispersibility of the powder may be useful. Carbohydrates/sugars and alditols are also useful. Suitable carbohydrate/sugar compounds include sucrose, trehalose, lactose, raffinose, and the like. Suitable alditols include mannitol and pyranosyl sorbitol and the like. Polymeric excipients/additives include polyvinylpyrrolidones (PVP), Ficolls, soluble hydroxy ethyl starch, dextrates and the like of high molecular weight. Also useful are small amounts of pharmaceutically acceptable surfactants such as Tweens, chelators such as EDTA and inorganic acids and bases such as sodium phosphate and the like. Other suitable pharmaceutical excipients and/or additives include those disclosed in Remington, Pharmaceutical Sciences 18th ed. (1990), the disclosure of which is incorporated herein by reference.

The temperatures employed for drying the atomized solution droplets may range from 20 to 300° C., preferably 30 to 150° C., and most preferably 40 to 120° C. These temperatures are expressed as the outlet temperature of the carrier gas. Specifically, the outlet temperature is the temperature of the gas at the outlet of the drying chamber prior to entry into the cyclone and collector. Correspondingly higher temperatures are required at the point of atomization to achieve the recommended outlet temperatures. The spray drying process may include maintaining the powder an additional period of time at a given temperature after the completion of cyclosporin solution feed through the system (i.e., secondary drying). This secondary drying may be used to reduce any residual solvent left in the powder.

A droplet size of about 4 to about 8 μm diameter is preferred in order to achieve optimal powder characteristics. Such a droplet size may be achieved, for example, by using the atomization method described in International Patent Application No. PCT/US97/07779. Unless otherwise specified, atomization methods that result in droplet sizes of 4–8 μm were used in the examples that follow.

The mass median diameter (MMD) of the powders prepared by organic spray drying were measured by centrifugal sedimentation with a Horiba CAPA-700 Particle Size Analyzer. A powder sample was dispersed in a vehicle of Sedisperse W-11 (Micromeritics, Norcross, Ga.) which was pre-saturated with cyclosporin A and filtered prior to the addition of the powder sample. The particle size ranged from about 0.7 to about 2.4 MMD. The size of the CsA particles was confirmed by scanning electron microscopy; the particles were also found to be generally spherical in shape, i.e., from smooth spheres to dimpled, raisin-like or wrinkled.

The aerosol performance characteristics of the powders were evaluated using the Inhale Therapeutic System's aerosol device. The device includes an aerosol chamber and employs a volume of compressed air to disperse the powder from an aluminum foil blister package. The delivered dose efficiency (DDE) for each powder was defined as the percentage of the nominal dose contained within a blister package that exited the mouthpiece of the aerosol device and was captured on a filter through which a vacuum was drawn (30 L/min) for 2.5 seconds following device actuation. The filter was weighed before and after actuation of the device to determine the mass of powder delivered past the mouthpiece. The particle size distribution of the aerosolized powders was determined using an Andersen cascade impactor through which a vacuum (28.3 L/min) was pulled for 2.5 seconds.

The residual solvent and/or moisture content of the powder particles of the present invention is usually below about 10% by weight, preferably below about 5% w and more preferably below about 3% w. Such low solvent and/or moisture content powders are generally physically and chemically stable during storage at room temperature and are readily dispersible in an inhalation device to form an aerosol.

Stability studies of spray dried cyclosporin formulations of the present invention were performed, and showed that these compositions retained aerosol and physical stability. In particular, the DDE of a cyclosporin powder spray dried from ethanol at 70° C. without secondary drying was measured immediately after preparation and found to be 48.4%. The powder was then stored at room temperature for 10 months. The DDE was again measured and found to be 49.5%, indicating that the powder retained aerosol stability.

In another stability test, the DDE of cyclosporin powders spray dried from ethanol at 70° C. without secondary drying was measured immediately after preparation and found to be about 72%. The powder was then stored at the accelerated conditions of 40° C. and 75% relative humidity (RH). DDE was measured after 8 weeks and again after 15 weeks of storage under these conditions. Results showed that the DDE remained approximately the same, i.e., about 75% at 8 weeks and about 74% at 15 weeks. A DSC scan of this powder formulation done immediately after preparation showed a melt at 118.61° C., while a DSC scan of the formulation done after 15 weeks at 40° C. and 75% relative humidity showed a melt at 119.00° C. These results indicate that no physical change of the powder occurred over this period and the powder retained aerosol stability.

The amount of cyclosporin which constitutes a therapeutically effective amount will vary in the composition depending on the biological activity of the cyclosporin employed and the amount needed in the unit dosage form. The condition to be treated or prevented will also determine the amount of cyclosporin required, as will the subject to which the composition is being administered. The compositions comprise at least about 40% by weight cyclosporin in the formulation, preferably between about 70% to about 100% and most preferably about 90% to about 100%. The amount of excipients and pharmaceutically acceptable additives may be from about 0–60%, preferably from about 0–30% and most preferably from about 0–10% by weight.

The compositions of the present invention will often be packaged as unit doses where a therapeutically effective amount of the cyclosporin composition is present in a unit dose receptacle, such as a blister pack, gelatin capsule, or the like, so long as a moisture barrier is provided.

The cyclosporin-based dry powder compositions of the present invention may be produced by spray drying solutions or slurries of the cyclosporin and, optionally, excipients, in a non-aqueous solvent under conditions to provide a respirable dry powder. Solvents may include ethanol, acetone, acetonitrile, methanol and isopropanol, which may be readily dried. Further, the cyclosporin-based dry powder compositions may also be produced by evaporative drying, freeze-drying, quench from a melt, precipitation including super-critical fluid precipitation.

C. Characterization:

It was found that, by spray drying cyclosporin from organic solvents, a thermotropic liquid crystal form of cyclosporin is formed. In particular, characterization of this cyclosporin form using polarized light microscopy, showed that it was birefringent, indicating that it was a non-amorphous form of cyclosporin. Similarly, SAXS analysis showed the presence of sharp peaks (FIG. 3), a characteristic of non-amorphous materials.

Further characterization of this novel form of cyclosporin by powder X-ray diffraction disclosed no sharp diffraction peaks which would have indicated a 3-dimensional order such as that found in crystalline structures, indicating that this was not a 3-dimensional crystalline form of cyclosporin. FIGS. 1A through 1C show X-ray powder diffraction patterns of two crystalline forms of cyclosporin (tetragonal and orthorhombic) and our novel spray dried form.

Hotstage microscopy, DSC, DEA, and SAXS were used to characterize the novel form of cyclosporin. Hotstage microscopy of this material showed a distinct melting point which is characteristic of both crystalline and liquid crystalline materials. DSC showed a step-wise heat capacity change at the melt temperature, characteristic of liquid crystalline materials. FIG. 2A shows a DSC (heating rate at 10° C./min) of the liquid crystal cyclosporin of the present invention, indicating a melting point beginning at 122° C. and which can be between 115° C. and 125° C. When analyzed by DEA, such transition was found to be frequency dependent, suggesting it is indeed a second order transition and not a true melt. The liquid crystal state was confirmed by SAXS, which showed sharp diffraction peaks at low diffraction angles, as characteristic of 2-dimensional order in liquid crystals. FIG. 3 shows SAXS for spray dried cyclosporin. The material remains a liquid crystal below the melt (at 10° C. and 80° C.) and above the melt (at 150° C.).

D. Pulmonary Cyclosporin

Pulmonary cyclosporin is useful for the treatment of asthma and lung transplants but has the potential for use in many other indications as well. Pulmonary cyclosporin may be useful to treat sarcoidosis. Obliterative bronchiolitis (OB), the pulmonary pathology that occurs in lung transplant rejection, also occurs in heart and bone marrow rejection, thus there is the potential for inhaled cyclosporin to be of use in other transplant therapies in conjunction with oral immunosuppressants. Chronic inflammatory lung disease, chronic obstructive pulmonary disease, emphysema, primary and secondary pulmonary hypertension, cystic fibrosis, lung infections or idiopathic pulmonary fibrosis (IPF) are other pulmonary diseases that may respond to inhaled cyclosporin, since they appear to be caused or exacerbated by an overly reactive immune system. Further, cyclosporin may be useful to treat pulmonary complications associated with autoimmune diseases such as rheumatoid arthritis. The advantage of pulmonary delivery of cyclosporin for lung disease or conditions which affect the lungs is that the total body burden of drug can be reduced, which reduces or eliminates systemic side effects.

According to the current invention, cyclosporin may be delivered directly to the deep lung in dry powder form using a dry powder delivery device. A significant requirement for such dry powder delivery devices is efficiency. The delivered dose must be relatively high to reduce the number of breaths required to achieve a total dosage. The ability to achieve adequate dispersion is a significant technical challenge that requires in part that each unit dosage of the powder composition be readily and reliably dispersible. Certain pulmonary delivery devices, such as those disclosed in U.S. Pat. No. 5,458,135 and International Patent Publication WO96/09085 (the disclosures of which are incorporated herein by reference) are useful for pulmonary delivery of dry powder drugs.

The disclosure of each of the publications, patents or patent applications herein mentioned is hereby incorporated by reference in its entirety to the same extent as if the language of each individual publication, patent and patent application was specifically and individually incorporated by reference.

DISCLOSURE OF THE EXAMPLES OF THE INVENTION

The following examples are not intended to limit the scope of the invention in any manner.

Materials and Methods:
In general the following materials and methods were used in the examples that follow unless otherwise indicated.
Materials:
Cyclosporin A, GMP grade, was obtained as a powder crystallized from acetone (melting point 148–150° C.) from Poli Industria Chimica, S.p.A.
Sample Storage:
Spray dried powders were stored under dry atmosphere (RH<5%).
Physical Methods:
Powder particle size distribution
The particle size distribution (PSD) of the spray dried powder samples was measured with a Horiba CAPA-700 centrifugal sedimentation particle size analyzer. A powder sample was dispersed in a vehicle of Sedisperse W-11 (Micromeritics, Norcross, Ga.) which was pre-saturated with cyclosporin A and filtered prior to the addition of the powder sample.

Figure 2B:
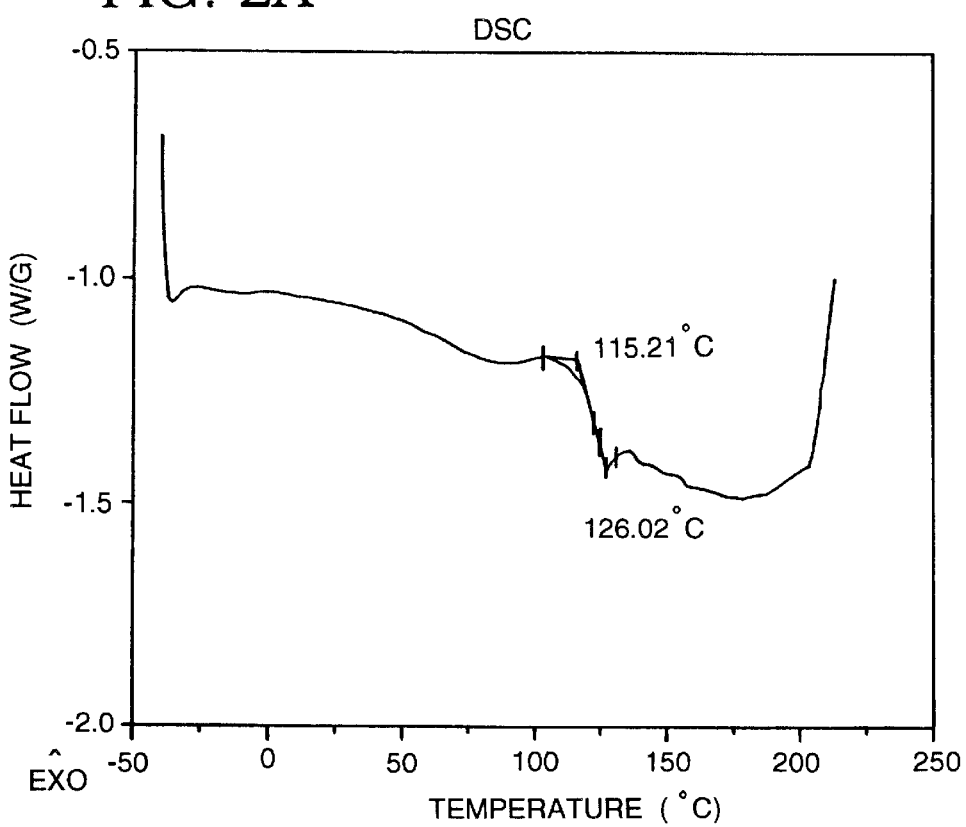

Approximately 5 mg of powder was suspended in about 5 ml of the Sedisperse and sonicated 5–10 minutes in a Lab Supplies ultra-sonicator before analysis. The instrument was configured to measure a particle size range of 0.4 to 10 $\mu$m in diameter using a particle density of about 1.2 g/cm$^3$.
Powder X-ray diffraction (PXRD)
The PXRD was performed on a Siemens D-500 X-ray Diffractor. The sample was measured at 3°/min (0.8 sec/ 0.04° step) and 0.5°/step, 1 sec/step respectively. The scan was run continuously from 2° to 40° in 2θ.
Small angle X-ray scattering (SAXS)
SAXS analysis was performed on a Rigaku 12KW diffractometer equipped with a Kratky camera and a Braun 10-cm position sensitive detector, using a copper X-ray source of 1.542 Å at a scanning rate of 0.12°/min in the range of 0 to 2.20° in 2θ.
Method to test birefringency
Birefringence was tested using a polarized light microscope, Nikon Optiphot 2-Pol, equipped with a Hamamatsu camera and controller C2400. Pictures were printed on a graphic printer UP890MD. The powders, either dry or immersed in Sedisperse W-11 or water, were examined under 20×, 40× and 60× objectives, and photomicrographs were taken through normal and cross polarized light.
Method for hotstage microscopy
Hotstage microscopy was performed on a Nikon Optiphot 2-Pol equipped with a Mettler Toledo FP82ITF Hotstage and a Hamamatsu camera and controller C2400. Photomicrographs were printed on a graphic printer UP890MD. The slide was placed in the hotstage and a representative field was found using the 40× objective. Samples were heated at a rate of 2° C./min from room temperature to past the melting point. Pictures were taken when changes were visually observed.
Method for TGA-Residual solvent
Samples were analyzed by Oneida Research Services, Inc. The TGA was performed on a Omnitherm 1500. Samples were heated from 30–200° C./min under a nitrogen atmosphere with a flow rate of 30 ml/min. The weight loss due to drying was measured and is presented as % weight lost.
Method for TGA-Decomposition
Samples were analyzed by Oneida Research Services, Inc. The TGA was performed on a Omnitherm 1500 TGA. Samples were heated from 40–600° C. at 10°/min under a nitrogen atmosphere with a flow rate of 30 ml/min.
Differential scanning calorimetry (DSC)
The DSC scans were performed on a TA Instrument model 2920 Modulated DSC with a TA refrigerated cooling system (RCS) unit, and pure helium gas with a flow rate of ~120 cm³/min. The cell flow rate was set at about 40 cm³/min. The scans were performed at 10° C./min non-modulated, with an equilibration temperature of −30° C. for 15–30 min, followed by heating to about 200–225° C. Open and closed aluminum pans were filled with about 2 mg–6 mg of powder (FIGS. 2A and 2B, respectively).

Dielectric analysis (DEA)

Figure 4:
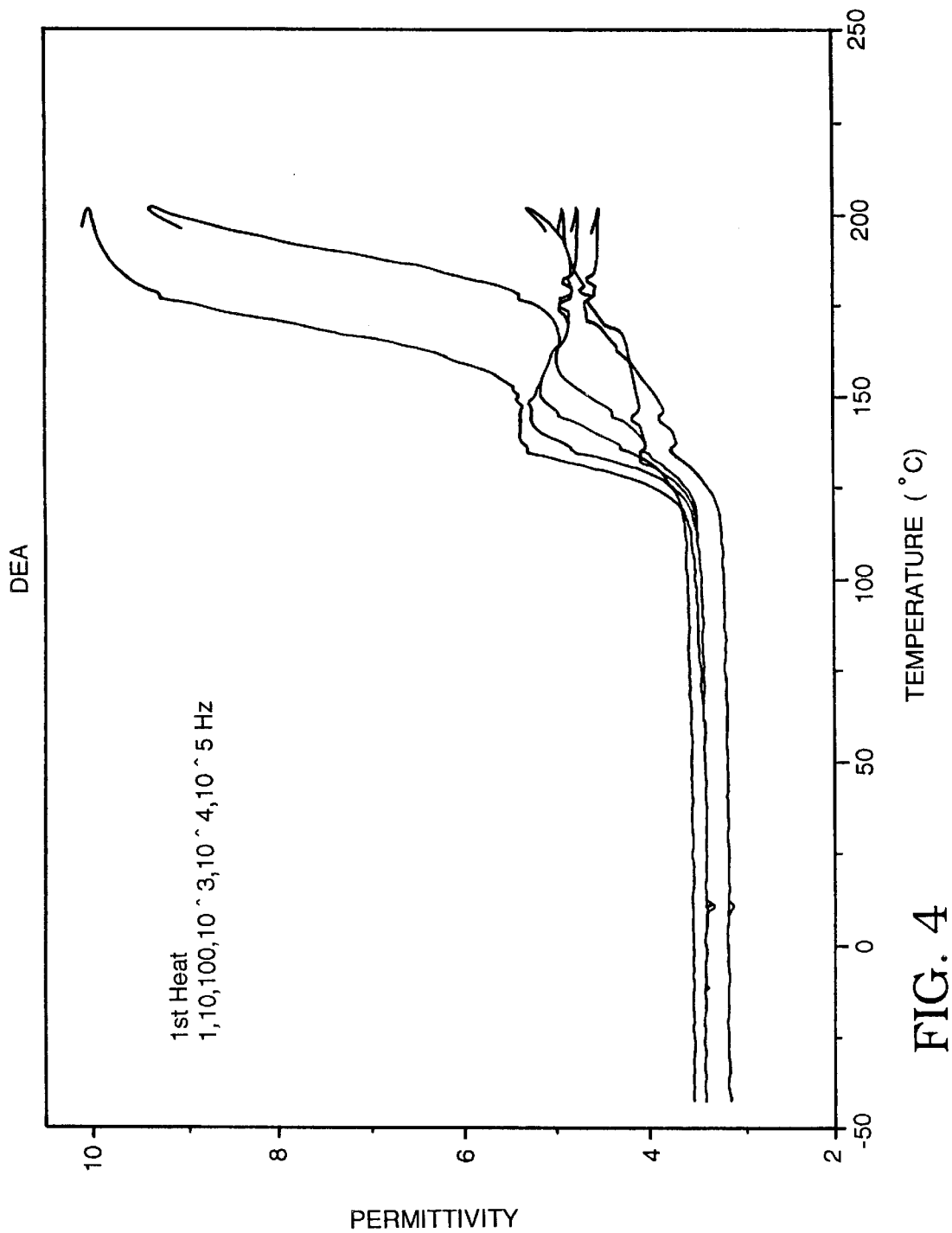
FIG. 4 presents the dielectric analysis (DEA) of a thermotropic liquid crystal CsA formulation according to the present invention.

The DEA scan was performed on a TA Instrument 2970 Dielectric Analyzer using liquid nitrogen to cool the sample to the initial temperature. The powder (40–45 mg) was pressed into a pellet, ½ inch in diameter and approximately 0.3 mm thick, using a Carver press for 40 seconds at 1 ton. Two thin layers of Teflon 25 $\mu$m and 7/16 inch in diameter, were inserted into the pellet die to alleviate adhesion to the die faces. During the measurement, the pellet was surrounded by a silicone gasket, ID 9/16 inch, OD 1 1/16 inches thickness, 0.35 mm, to help maintain thickness during the measurement. The pellet was also sandwiched between two layers of Teflon, 25 $\mu$m thick, to remove possible contributions from ionic conductivity. Electrodes were fabricated from TA Instruments' sensors for sputter coated samples and gold foil, 25 $\mu$m thick, one disk 7/16 inch in diameter and the other 5/8 inch in diameter, so that only the sample contacted the foil electrodes. Experiments were performed using a heating rate of 2° C./min from −40 to 200° C. and using the following frequencies: 1 Hz, 10 Hz, 100 Hz, 1,000 Hz, 10,000 Hz, 100,000 Hz. The permitivities measured with this method were in arbitrary units since the data was not adjusted for the gold foil sensors; however, this does not impact the interpretation of the results (FIG. 4).

Aerosol Methods:

Delivered dose assay

The delivered dose assay was performed to determine the efficiency and reproducibility of pulmonary delivery of the dispersible powder cyclosporin compositions. The aerosol performance characteristics of the powders were evaluated using the Inhale Therapeutic System's aerosol device, similar to devices disclosed in WO96/09085. The device includes an aerosol chamber and employs a volume of compressed air to disperse the powder from an aluminum foil blister package. The delivered dose efficiency (DDE) for each powder was defined as the percentage of the nominal dose contained within a blister package that exited the mouthpiece of the aerosol device and was captured on a glass fiber filter (Gelman, 47 mm diameter) through which a vacuum was drawn (30 L/min) for 2.5 seconds following device actuation. Delivered dose efficiency was calculated by dividing the mass of the powder collected on the filter by the mass of the powder in the blister pack. Each result was the average of 5–10 replicate measurements.

Aerosol particle size distribution

The aerosol particle size distribution was obtained using an eight stage cascade impactor (Graseby Andersen, Smyrna, Ga.). The impactor air-flow was set to pull a vacuum of 28.3 L/min, the calibrated flow-rate for the instrument, for 2.5 seconds. For each run, the blister packs filled with approximately 5 mg of powder were dispersed from the inhaler. The particle size was determined by weighing the powder on the impactor plates and evaluating the results on a log-probability plot. Both the mass median aerodynamic diameter (MMAD) and the mass fraction less than 5 $\mu$m were determined from the log-probability plot.

Chemical Stability Method:

The stability-indicating HPLC method that was used is described in Oliyai, et al., Kinetics of Acid-Catalyzed Degradation of Cyclosporin A and its Analogs in Aqueous Solutions, Peptide and Protein Res. 43:239–247 (1994). The method was run according to that described, however the mobile phase ratio was adjusted slightly to obtain the retention times for cyclosporin A and iso-cyclosporin A.

EXAMPLE 1

Cyclosporin A Spray Dried From Ethanol At 70° C. With No Secondary Drying

Solution Preparation 1.5 g of cyclosporin A was dissolved in 50 mL of ethanol (200 proof, USP, NF grade from Spectrum).

Spray Drying

A dry powder comprised of cyclosporin A was produced by spray drying the organic solution using a Buchi B-190 Laboratory Spray Dryer using a nitrogen atmosphere containing less than 5% oxygen (with $N_2$ atm<5% $O_2$) with the following parameters:

| | |
|---|---|
| Outlet Temperature | 70° C. |
| Inlet Temperature | 100° C. |
| Feed Rate | 5 mL/min |
| Atomizer Flow Rate | 13 lit/min |
| Secondary Drying | None |

Powder Characterization

PXRD of the powder showed that it exhibited a double halo with two maxima at 2θ equal to 8.5° and 17° (FIG. 1C). The absence of sharp peaks in the diffractogram show that the material is not a 3-dimensional crystal. Polarized light microscopy showed the particles to be birefringent. The SEM images appear to be rounded and highly wrinkled particles. There was no solid state change in the formulation due to the increase in relative humidity as shown by the DSC's of the powders exposed to 0% relative humidity and 75% relative humidity. The DSC scan showed a large endotherm ranging from about 20° C. to about 70° C. with a peak maximum at 69° C. The Tg-like endotherm, which is a melt, appeared on the scan at 122° C. onset temperature. Hotstage microscopy showed the melt to be in the range of 138–140° C. The MMD of the powder sample was determined to be 1.6 $\mu$m, with 96.5% less than 5.2 $\mu$m.

The DEA showed a frequency-dependent change in the permitivity indicative of a second order transition, in the same temperature range as determined by DSC, where the change in heat capacity started around 125° C. At the temperature range that the large endotherm was seen in the DSC scan (~20–70° C.), there was no change in the permitivity, suggesting that the endotherm is not due to a phase change but rather to solvent evaporation.

Aerosol Characterization

The delivered dose efficiency (DDE) of the above spray dried cyclosporin A powder was determined to be 79%±4.2% (n=10). The mass median aerodynamic diameter (MMAD) was determined to be 2.81 $\mu$m, with 85% less than 5 $\mu$m.

Chemical Stability

Figure 5C:
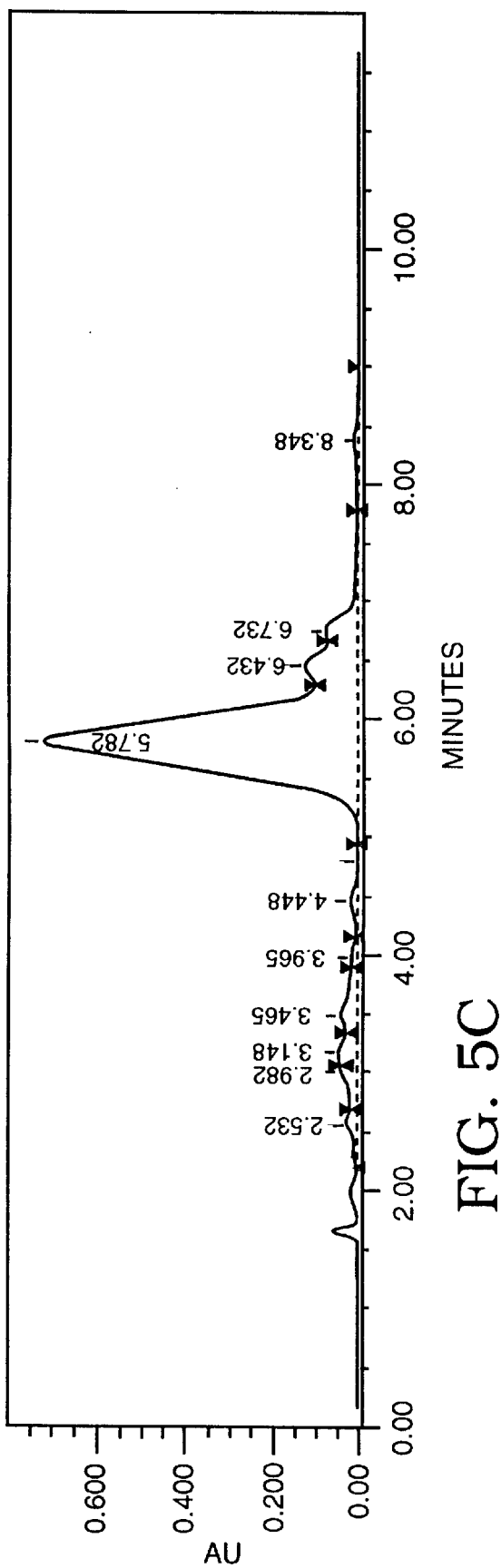

HPLC analysis showed degradation products of the spray dried cyclosporin A under stressed conditions. FIG. 5A shows a sample stored at 110° C. for 196 hours, FIG. 5B shows a sample stored at 140° C. for 50 hours and FIG. 5C shows a sample stored at 210° C. for 10 minutes. The degradation products for the liquid crystal cyclosporin are different than for other reported forms of cyclosporin. (Oliyai, et al., Kinetics of Acid-Catalyzed Degradation of Cyclosporin A and its Analogs in Aqueous Solution, Peptide and Protein Res. 43:239–247 (1994) and Oliyai, et al., Kinetics and Mechanism of Isomerization of Cyclosporin A, Pharm. Res. 9(5):617–622 (1992)).

EXAMPLE 2

Cyclosporin A Spray Dried From Acetone At 88° C. With Secondary Drying

Solution Preparation 1.5 g of cyclosporin A was dissolved in 50 nL of acetone (HPLC grade from J. T. Baker).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 88° C. |
| Inlet Temperature | 118° C. |
| Feed Rate | 5 mL/min |
| Atomizer Flow Rate | 13 lit/min |
| Secondary Drying | 85° C./5 min |

Once the solution was consumed, the outlet temperature was maintained at 85° C. for 5 min by slowly decreasing the inlet temperature to provide secondary drying.

Powder Characterization

PXRD of the powder showed that it exhibited a double halo with two maxima at 2θ equal to 8.5° and 17°. Polarized light microscopy showed the particles to be birefringent. TGA analysis of the powder showed the powder to have 0.1% by weight of residual solvent and a decomposition temperature range of 347–421° C. The SEM image of the powder showed the particles to be rounded, with slight dimples. The DSC scan showed a large endotherm ranging from about 20° C. to about 70° C. with a peak maximum at 58° C. The Tg-like endotherm, which is a melt, appeared on the scan at 121° C. onset temperature. The MMD of the powder sample was determined to be 1.19 μm, with 95.8% less than 5.2 μm.

Aerosol Characterization

The DDE of the above spray dried cyclosporin A powder was determined to be 59%±9% (n=10). The MMAD was determined to be 2.0 μm with 84% less than 5 μm.

EXAMPLE 3

Cyclosporin A Spray Dried From Ethanol At 85° C. With Secondary Drying

Solution Preparation 1.5 g of cyclosporin A was dissolved in 50 mL of ethanol (200 proof, USP, NF grade from Spectrum).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 85° C. |
| Inlet Temperature | 120° C. |
| Feed Rate | 5 mL/min |
| Atomizer Flow Rate | 13 lit/min |
| Secondary Drying | 85° C./5 min |

Once the solution was consumed, the outlet temperature was maintained at 85° C. for 5 min by slowly decreasing the inlet temperature to provide secondary drying.

Powder Characterization

PXRD of the powder showed that it exhibited a double halo with two maxima at 2θ equal to 8.5° and 17°. Polarized light microscopy showed the particles to be birefringent. TGA analysis of the powder showed the powder to have 0.3% by weight of residual solvent and a decomposition temperature range of 348–425° C. The SEM image of the powder showed the particles were raisin-like. The DSC scan showed a large endotherm ranging from about 20° C. to about 70° C. with a peak maximum at 62° C. The Tg-like endotherm, which is a melt, appeared on the scan at 122° C. onset temperature. The MMD of the powder sample was determined to be 1.27 μm, with 100% less than 5.2 μm.

Aerosol Characterization

The DDE of the above spray dried cyclosporin A powder was determined to be 71.4%±6% (n=10). The NMAD was determined to be 2.8 Jim with 86% less than 5 μm.

Chemical Stability

Figure 6A:
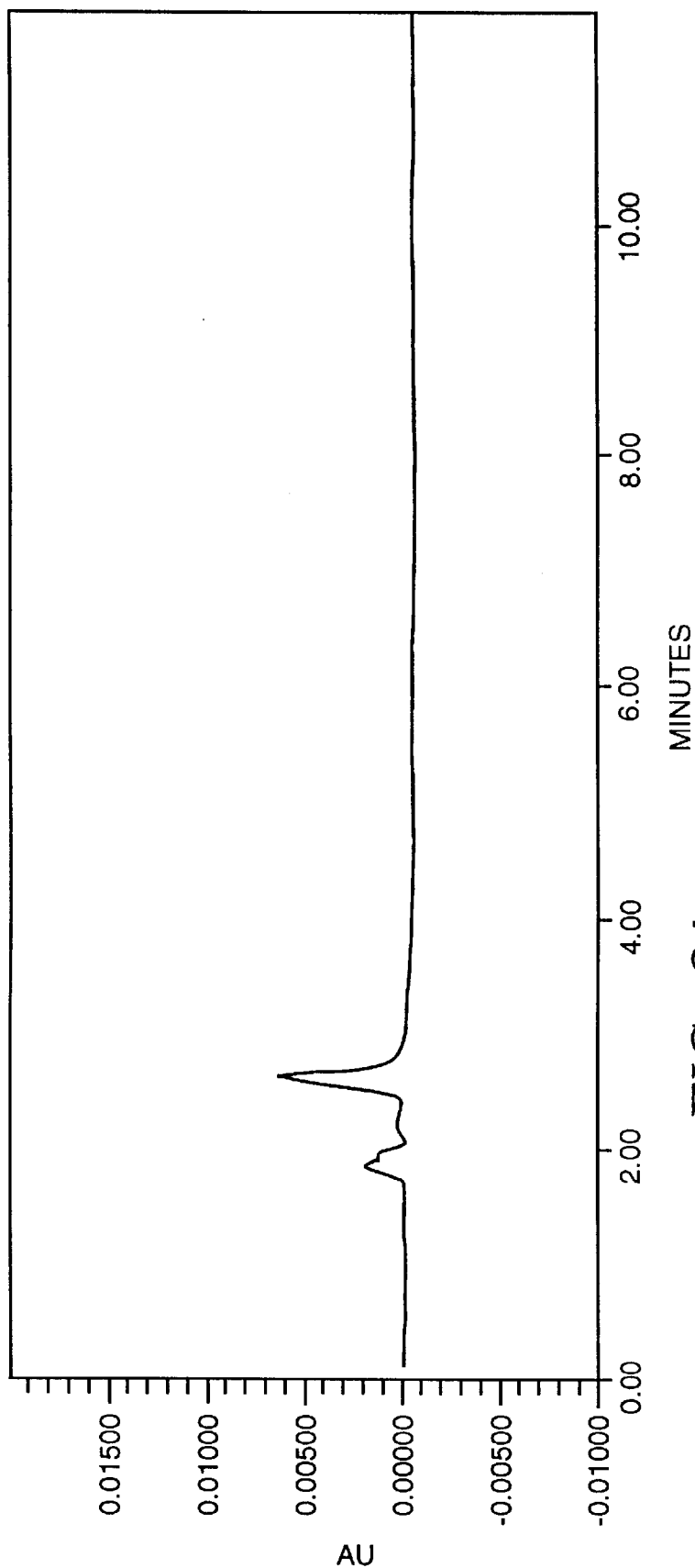
FIGS. 6A, 6B and 6C demonstrate that spray dried cyclosporin A powder stored for 10 months at 40° C. and 75% relative humidity that showed no appreciable degradation based on HPLC analysis.
Figure 6B:
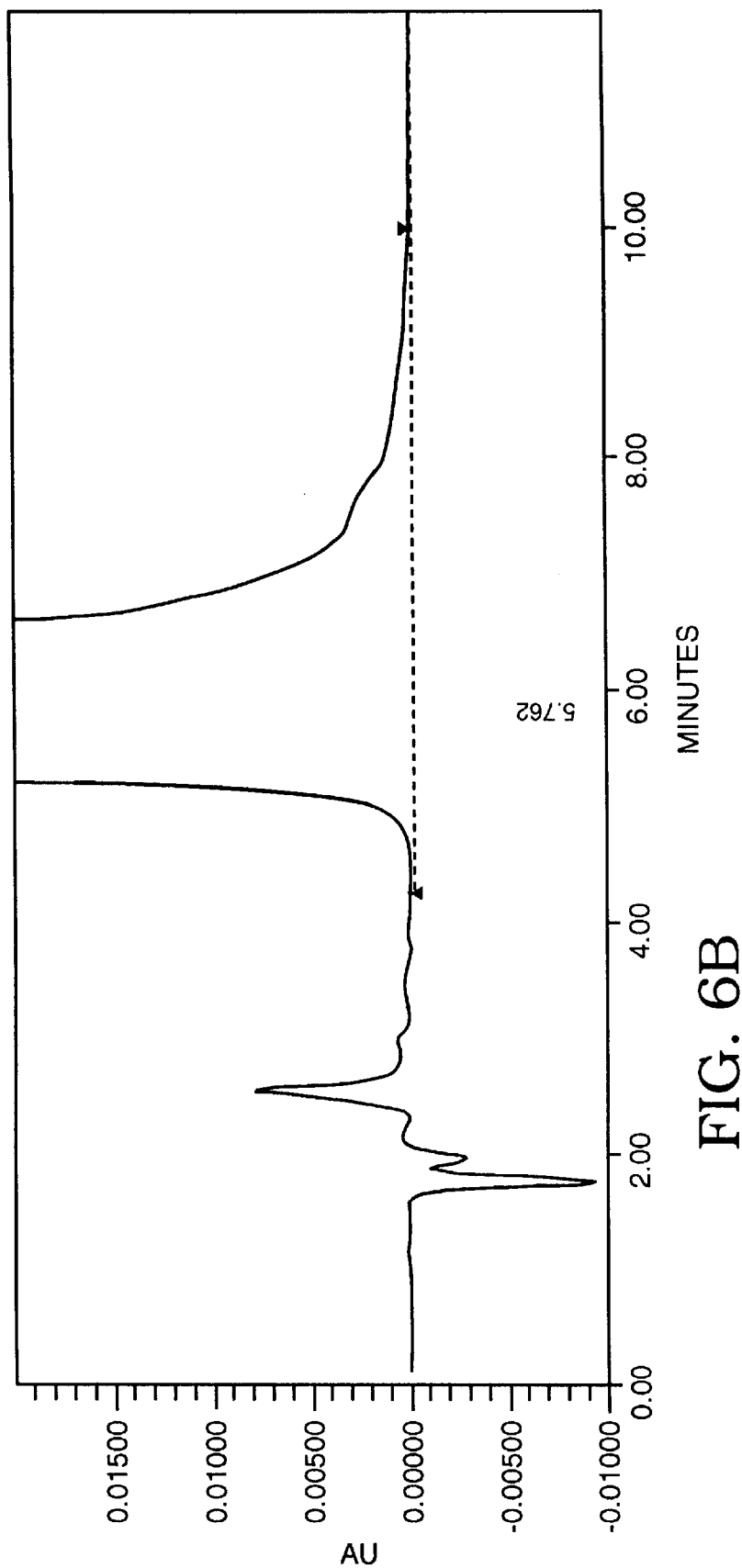
Figure 6C:
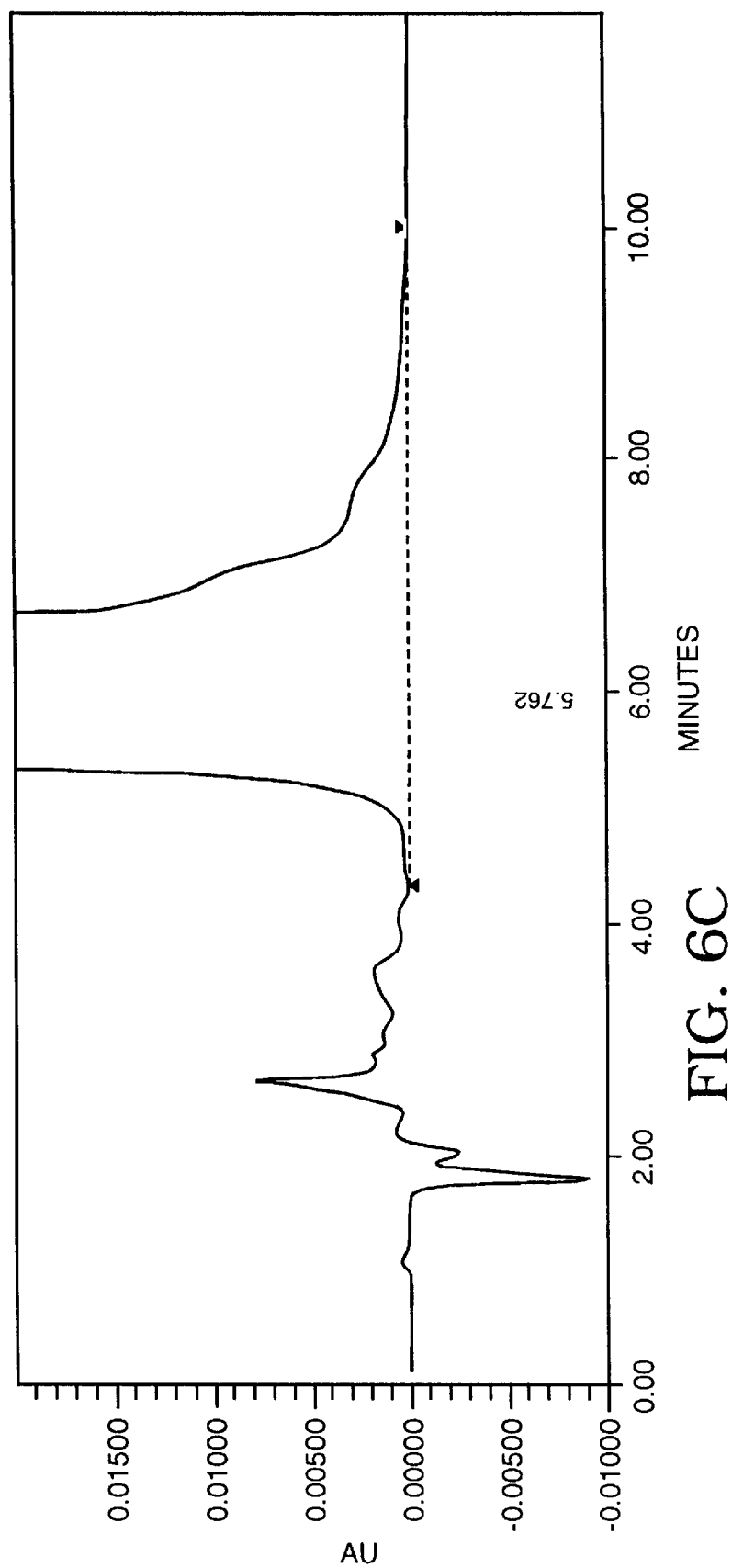

HPLC analysis showed no appreciable degradation from samples of the spray dried cyclosporin A powder stored at 40° C. and 75% relative humidity for 10 months (see FIGS. 6A, 6B and 6C). The powder is considered to be chemically stable over the time course of the study. FIG. 6A is a chromatogram of the mobile phase, FIG. 6B is a chromatogram of the bulk cyclosporin A in the mobile phase with a 25 μg load. FIG. 6C is a chromatogram of the spray dried cyclosporin A aged at 40° C. and 75% relative humidity for 10 months reconstituted in the mobile phase.

EXAMPLE 4

Cyclosporin A Spray Dried From Acetonitrile At 101° C. With Secondary Drying

Solution Preparation 1.5 g of cyclosporin A was dissolved in 50 mL of acetonitrile (HPLC grade from Burdick and Jackson).

Spray Drying

A dry powder comprised of cyclosporin A was produced by spray drying the organic solution using a Buchi B-190 Laboratory Spray Dryer with $N_2$ atm<5% 02 with the following parameters:

| | |
|---|---|
| Outlet Temperature | 101° C. |
| Inlet Temperature | 141° C. |
| Feed Rate | 5 mL/min |
| Atomizer Flow Rate | 15 lit/min |
| Secondary Drying | 100° C./5 min |

Once the solution was consumed, the outlet temperature was maintained at 100° C. for 5 min by slowly decreasing the inlet temperature to provide secondary drying.

Powder Characterization

PXRD of the powder showed that it exhibited a double halo with two maxima at 2θ equal to 8.5° and 17°. Polarized light microscopy showed the particles to be birefringent. The SEM image of the powder showed the particles to be slightly dimpled. The DSC scan showed a large endotherm ranging from about 20° C. to about 70° C. with a peak maximum at 69° C. The Tg-like endotherm, which is a melt, appeared on the scan at 121° C. onset temperature. The My of the powder sample was determined to be 1.99 μm, with 99% less than 5.2 μm.

Aerosol Characterization

The DDE of the above spray dried cyclosporin A powder was determined to be 69.9%±7% (n=10). The MMAD was determined to be 1.9 μm with 83% less than 5 μm.

EXAMPLE 5

Cyclosporin A Spray Dried From Acetone At 102–103° C. With Secondary Drying

Solution Preparation 1.5 g of cyclosporin A was dissolved in 50 mL of acetone (HPLC grade from J. T. Baker).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 102–103° C. |
| Inlet Temperature | 140° C. |
| Feed Rate | 5 mL/min |
| Atomizer Flow Rate | 15 lit/min |
| Secondary Drying | 101° C./5 min |

Once the solution was consumed, the outlet temperature was maintained at 101° C. for 5 min by slowly decreasing the inlet temperature to provide secondary drying.

Powder Characterization

Polarized light microscopy showed the particles to be birefringent. The SEM image of the powder showed that the particles looked round. The DSC scan showed a large endotherm ranging from about 20° C. to about 70° C. with a peak maximum at 69° C. The Tg-like endotherm, which is a melt, appeared on the scan at 123° C. onset temperature.

The MMD of the powder sample was determined to be 1.20 μm with 87.0%<5.2 μm.

Aerosol Characterization

The DDE of the above spray dried cyclosporin A powder was determined to be 63.3%±7% (n=10). The MMAD was determined to be 1.8 μm with 80% less than 5 μm.

EXAMPLE 6

90% Cyclosporin A:10% Citrate Spray Dried From Ethanol At 85° C. With Secondary Drying Solution Preparation 1.35 g of cyclosporin A was dissolved in 50 mL of ethanol (200 proof, USP, NF grade from Spectrum). 150 mg of Sodium Citrate from Sigma Chemicals was dissolved in 2.5 mL of de-ionized water. The ethanol/cyclosporin A solution was added to the Sodium Citrate/water solution and swirled rapidly. The resulting suspension was processed in the Spray Dryer.

Spray Drying

A dry powder comprised of cyclosporin A and sodium citrate (90:10) was produced by spray drying the organic solution using a Buchi B-190 Laboratory Spray Dryer with $N_2$ atm<5% $O_2$ with the following parameters:

| | |
|---|---|
| Outlet Temperature | 85° C. |
| Inlet Temperature | 120° C. |
| Feed Rate | 5 mL/min |
| Atomizer Flow Rate | 13 lit/min |
| Secondary Drying | 85° C./5 min |

Once the solution was consumed, the outlet temperature was maintained at 85° C. for 5 min by slowly decreasing the inlet temperature to provide secondary drying.

Powder Characterization

PXRD of the powder showed that it exhibited a double halo with two maxima at 2θ equal to 8.5° and 17°. The sharp diffraction peaks which stood out above the double halo corresponded to a sodium citrate dihydrate scan. Polarized light microscopy showed the particles to be birefringent. TGA analysis of the powder showed the powder to have 1.3% by weight of residual solvent and a decomposition temperature range of 288–395° C. The SEM image of the powder showed the particles appeared raisin-like and some facetted individual citrate crystals were observed. The DSC scan showed a large endotherm ranging from about 20° C. to about 70° C. with a peak maximum at 59° C. The Tg-like endotherm, which is a melt, appeared on the scan at 117° C. onset temperature. The MMD of the powder sample was determined to be 1.11 μm, with 96.7% less than 5.2 μm.

Aerosol Characterization

The DDE of the above spray dried cyclosporin A:citrate (90:10) powder was determined to be 65.9%±5% (n=10). The MMAD was determined to be 3.2 μm with 78% less than 5 μm.

EXAMPLE 7

Cyclosporin A Spray Dried From Ethanol At 85° C. Without Secondary Drying

Solution Preparation 1.5 g of cyclosporin A was dissolved in 50 mL of ethanol (200 proof, USP, NF grade from Spectrum).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 85° C. |
| Inlet Temperature | 120° C. |
| Feed Rate | 5 mL/min |
| Atomizer Flow Rate | 13 lit/min |
| Secondary Drying | None |

Powder Characterization

PXRD of the powder showed that it exhibited a double halo with two maxima at 2θ equal to 8.5° and 17°. Polarized light microscopy showed the particles to be birefringent. TGA analysis of the powder showed the powder to have 0.7% by weight of residual solvent and a decomposition temperature range of 347–428° C. The SEM image of the powder showed that the particles looked raisin-like. The DSC scan showed a large endotherm ranging from about 20° C. to about 70° C. with a peak maximum at 65° C. The Tg-like endotherm, which is a melt, appeared on the scan at 122° C. onset temperature. The MMD of the powder sample was determined to be 0.9 μm, with 97.6% less than 5.2 μm.

Aerosol Characterization

The DDE of the above spray dried cyclosporin A powder was determined to be 70.8%±3% (n=10). The NMAD was determined to be 2.7 μm with 85% less than 5 μm.

EXAMPLE 8

Cyclosporin A Spray Dried From Ethanol At 101° C. With No Secondary Drying

Solution Preparation 1.0 g of cyclosporin A was dissolved in 33 ml of ethanol (BPLC grade).

Spray Drying

A dry powder comprised of cyclosporin A was produced by spray drying the organic solution using a Buchi B-190

Laboratory Spray Dryer with N$_2$ atm<5% O$_2$ with the following parameters:

| | |
|---|---|
| Outlet Temperature | 101° C. |
| Inlet Temperature | 138° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were slightly dimpled. The DSC scan showed a large endotherm ranging from about 20° C. to about 70° C. with a peak maximum at 68° C. The Tg-like endotherm, which is a melt, appeared on the scan at 122° C. onset temperature. The MMD of the powder sample was determined to be 2.3 μm, with 86.6% less than 5.2 μm. The X-ray diffraction pattern of the powder showed a halo with two broad maxima at 2θ equal to ~8.5° and ~18.8°. The small angle X-ray diffraction pattern of the powder showed a peak at 2° equal to 0.2°, indicative of 2-dimensional order.

Aerosol Characterization

The DDE of the above spray dried cyclosporin A powder was determined to be 64%±6.9% (n=7). The MMAD was determined to be 2.59 μm with 75% less than 5 μm.

EXAMPLE 9

Cyclosporin A Spray Dried From Acetone At 49° C. With No Secondary Drying

Solution Preparation 1.0 g of cyclosporin A was dissolved in 33 mL of acetone (HPLC grade).

Spray Drying

A dry powder comprised of cyclosporin A was produced by spray drying the organic solution using a Buchi B-190 Laboratory Spray Dryer with N$_2$ atm<5% O$_2$ with the following parameters:

| | |
|---|---|
| Outlet Temperature | 49° C. |
| Inlet Temperature | 60° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were round and dimpled. The MMD of the powder sample was determined to be 3.5 μm, with 70.3% less than 5.2 μm.

Aerosol Characterization

The DDE of the above spray dried cyclosporin A powder was determined to be 52.4%±2.1% (n=7). The MMAD was determined to be 2.30 ym with 63.6% less than 5 μm.

EXAMPLE 10

Cyclosporin A Spray Dried From Acetone At 100° C. With No Secondary Drying

Solution Preparation 1.0 g of cyclosporin A was dissolved in 33 mL of acetone (HPLC grade).

Spray Drying

A dry powder comprised of cyclosporin A was produced by spray drying the organic solution using a Buchi B-190 Laboratory Spray Dryer with N$_2$ atm<5% O$_2$ with the following parameters:

| | |
|---|---|
| Outlet Temperature | 100° C. |
| Inlet Temperature | 135° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were round and non-dimpled. The DSC scan showed a large endotherm ranging from about 20° C. to about 70° C. with a peak maximum at 66° C. The Tg-like endotherm, which is a melt, appeared on the scan at 120° C. onset temperature. The MMD of the powder sample was determined to be 2.75 μm, with 76.3% less than 5.2 μm.

The X-ray diffraction pattern of the powder showed a halo with a broad maxima at 2θ equal to ~7.80. The small angle X-ray diffraction pattern of the powder showed a peak at 2θ equal to 0.2°, indicative of 2-dimensional order.

Aerosol Characterization

The delivered dose efficiency (DDE) of the above spray dried cyclosporin A powder was determined to be 57.3%±3.42% (n=7). The mass median aerodynamic diameter (MMAD) was determined to be 2.1 gn with 70% less than 5 μm.

EXAMPLE 11

Cyclosporin A Spray Dried From Isopropanol At 77° C., No Secondary Drying

Solution Preparation 1.0 g of cyclosporin A was dissolved in 33 mnL of isopropyl alcohol (HPLC grade).

Spray Drying

A dry powder comprised of cyclosporin A was produced by spray drying the organic solution using a Buchi B-190 Laboratory Spray Dryer with N$_2$ atm<5% O$_2$ with the following parameters:

| | |
|---|---|
| Outlet Temperature | 77° C. |
| Inlet Temperature | 105° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were round and slightly dimpled. The DSC scan showed a large endotherm ranging from about 20° C. to about 70° C. with a peak maximum at 66° C. The Tg-like endotherm, which is a melt, appeared on the scan at 122° C. onset temperature. The MMD of the powder sample was determined to be 2.22 gm, with 85.7% less than 5.2 μm. The X-ray diffraction pattern of the powder showed a halo with a broad maxima at 2θ equal to ~7.5°. The small angle X-ray diffraction pattern of the powder showed a peak at 2θ equal to 0.1°, indicative of 2-dimensional order.

Aerosol Characterization

The DDE of the above spray dried cyclosporin A powder was determined to be 69.2%±2.42% (n=7). The MMAD was determined to be 3.8 μm with 97.8% less than 5 μm.

EXAMPLE 12

Cyclosporin A Spray Dried From Isopropanol At 104° C., No Secondary Drying

Solution Preparation 1.0 g of cyclosporin A was dissolved in 33 mL of isopropyl alcohol (BPLC grade).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 104° C. |
| Inlet Temperature | 145° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were round and non-dimpled. The DSC scan showed a large endotherm ranging from about 20° C. to about 70° C. with a peak maximum at 66° C.

The Tg-like endotherm, which is a melt, appeared on the scan at 121° C. onset temperature. The MMD of the powder sample was determined to be 2.36 μm, with 89.9% less than 5.2 μm. The X-ray diffraction pattern of the powder showed a halo with two broad maxima at 2θ equal to ~8.9° and ~19°. The small angle X-ray diffraction pattern of the powder showed a peak at 2θ equal to 0.1°, indicative of 2-dimensional order.

Aerosol Characterization

The DDE of the above spray dried cyclosporin A powder was determined to be 67.1%±2.85% (n=7). The MMAD was determined to be 2.7 μm with 76.8% less than 5 μm.

EXAMPLE 13

Cyclosporin A Spray Dried From Methanol At 63° C. With No Secondary Drying

Solution Preparation 1.0 g of cyclosporin A was dissolved in 33 mL of methanol (HPLC grade).

Spray Drying

A dry powder comprised of cyclosporin A was produced by spray drying the organic solution using a Buchi B-190 Laboratory Spray Dryer with $N_2$ atm<5% $O_2$ with the following parameters:

| | |
|---|---|
| Outlet Temperature | 63° C. |
| Inlet Temperature | 88° C. |
| Feed Rate | 5 mL/min |
| Atomizer Flow Rate | 14.5 lit/min |
| Secondary Drying | None |

Powder Characterization

Polarized light microscopy showed the particles to be birefringent. The SEM images showed that the particles were very dimpled. The MMD of the powder sample was determined to be 2.37 μm, with 90.1% less than 5.2 μm. The DSC scan showed a large endotherm ranging from about 20–70° C. with a peak maximum at 52° C. The Tg-like endotherm, which is a melt, appeared on the scan at 119° C. onset temperature.

Aerosol Characterization

The DDE of the above spray dried cyclosporin A powder was determined to be 67.2%±3.43% (n=6). The MMAD was determined to be 2.5 ym with 80.7% less than 5 μm.

EXAMPLE 14

The method of Example 1 was followed except that the solution was atomized using a standard, commercially available, Buchi nozzle. The mass mean diameter (MMD) of the droplets using this nozzle was between 7 and 15 μm.

Chemical Stability

Figure 7:
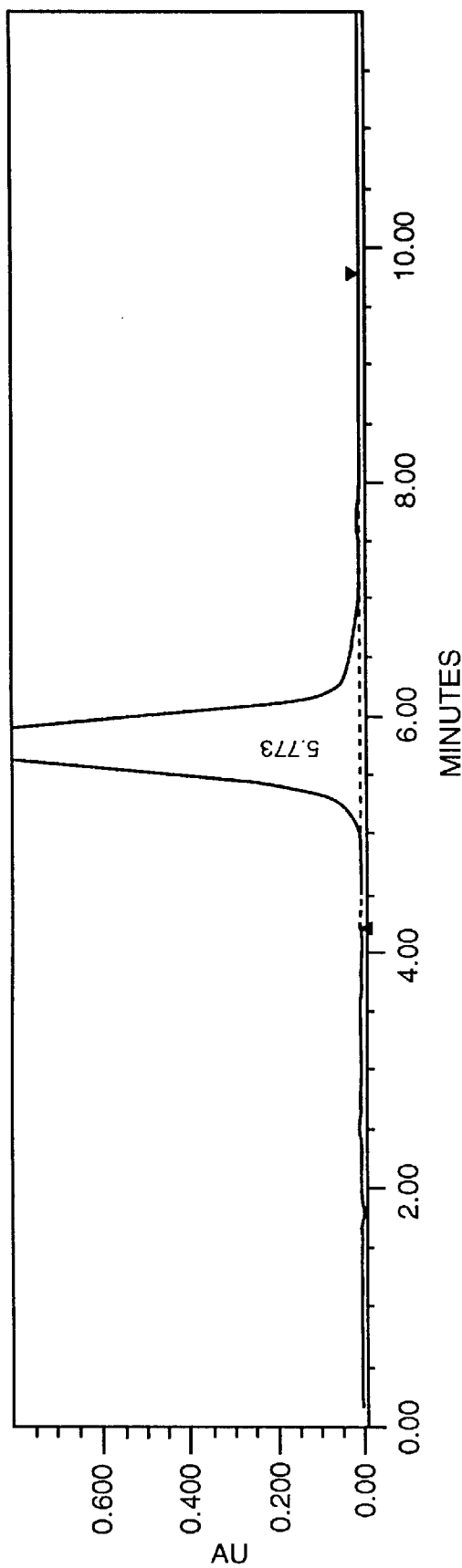
FIG. 7 demonstrates that spray dried cyclosporin A powders stored at room temperature for 15 months that showed no appreciable degradation based on HPLC analysis.

HPLC analysis showed no appreciable degradation from the samples of the spray dried cyclosporin A powder. FIG. 7 is a chromatogram of the spray dried sample reconstituted in a mobile phase after storage for 15 months at room temperature. The powder was determined to be chemically stable over the time course of the study.

EXAMPLE 15

Processing of Spray Dried Cyclosporin A Powder Formulations

Spray dried cyclosporin A powders were produced from various solvents using a variety of spray drying temperatures with or without secondary drying. Secondary drying appeared to have no effect on particle properties.

Measurement of residual solvent showed that little solvent was left in the particles. Lower levels of residual solvent are preferred to minimize any possible lung irritation caused by solvent.

The percent yield, defined as the weight of CsA-containing powder recovered in the collector of the spray dryer divided by the weight of CsA (and any excipient) in the solution which was spray dried (times 100%), ranged from 22% to 78%. Yields of at least about 20% are preferred, with higher yields being generally more preferred, so long as other powder characteristics such as MMD and DDE are acceptable.

The fine particle fraction (%), defined as DDE times the %<5 μm, ranged from 33.3 to 67.7%. Powders with a fine particle fraction of at least about 25% are preferred.

Several batches of CsA powders were spray dried from ethanol at 70° C. without secondary drying. The results of these batches is presented in Table 2.

TABLE 2

CsA Powders Spray Dried from Ethanol at 70° C. with No Secondary Drying

| Trial | Yield % | MMD μm | DDE % | % <5 μm | Fine Particle Fraction |
|---|---|---|---|---|---|
| 1 | 70.0 | 0.8 | 71.4 | 85.6 | 61.1 |
| 2 | 66.3 | 1.6 | 78.6 | 84.4 | 66.4 |
| 3 | 59.5 | 1.7 | 76.3 | 78.0 | 59.5 |

Modification of the above-described modes of carrying out the various embodiments of this invention will be apparent to those skilled in the art following the teachings of this invention as set forth herein. The examples described above are not limiting, but are merely exemplary of this invention, the scope of which is defined by the following claims.

The disclosure of each publication, patent or patent application mentioned in this specification is hereby incorporated by reference to the same extent as if each individual publication, patent or patent application were specifically and individually indicated to be incorporated by reference.

It is claimed:

1. Cyclosporin in thermotropic liquid crystal form.

2. The cyclosporin of claim 1 wherein the cyclosporin is cyclosporin A.

3. The cyclosporin of claim 1 which shows sharp peaks by small angle X-ray scattering.

4. The cyclosporin of claim 1 which is in dispersible powder form.

5. The cyclosporin of claim 1 which is prepared by spray drying from a solvent.

6. A composition for pulmonary delivery comprising thermotropic liquid crystal cyclosporin in respirable powder particles.

7. The composition of claim 6 wherein the cyclosporin is cyclosporin A.

8. The composition of claim 6 which is dispersible.

9. The composition of claim 6 which further comprises a pharmaceutically acceptable excipient or carrier.

10. The composition of claim 6 which is prepared by spray drying.

11. The composition of claim 6 wherein the cyclosporin comprises at least about 40% by weight of the composition.

12. The composition of claim 6 wherein the particles in the powder have a particle size range between 0.1 and 15 μm MMD.

13. The composition of claim 6 wherein the particles have an MMAD of less than about 5 μm.

14. The composition of claim 6 which has a delivered dose efficiency of at least about 30%.

15. A method for preparing the composition of claim 6 comprising:
   a) mixing cyclosporin with a solvent to form a solution or suspension; and
   b) spray drying the solution or suspension formed in step a) under conditions which provide a respirable powder.

16. The method of claim 15 further comprising the step of adding a pharmaceutically acceptable excipient or carrier prior to spray drying.

17. The method of claim 16 wherein said solvent comprises a solution of less than 50% water.

18. The method of claim 15 wherein the solvent is selected from the group consisting of ethanol, acetone, acetonitrile, isopropanol and methanol.

19. A method of treating a condition in a subject which is treatable by administration of cyclosporin, the method comprising pulmonary administration of a therapeutically effective amount of the composition of claim 6 to a subject suffering from the condition.

20. The method of claim 19 wherein the condition is selected from the group consisting of asthma, transplant rejection, sarcoidosis, chronic inflammatory lung disease, chronic obstructive pulmonary disease, emphysema, primary and secondary pulmonary hypertension, cystic fibrosis, lung infections, rheumatoid arthritis and idiopathic pulmonary fibrosis.

21. A method for preparing the composition of claim 1, comprising:
   a) mixing cyclosporin with a solvent to form a solution or suspension; and
   b) spray drying the solution or suspension formed in step a) to form cyclosporin in liquid crystal form.

22. The method of claim 21 wherein said cyclosporin formed in step b) is in the form of a thermotropic liquid crystal.

23. A method for delivery of cyclosporin to the lungs of a subject, said method comprising administering by inhalation the composition of claim 6 in aerosolized form.

24. The cyclosporin of claim 4 in aerosolized form.

* * * * *